United States Patent
Rudolph et al.

(10) Patent No.: US 8,709,104 B2
(45) Date of Patent: Apr. 29, 2014

(54) DYE-ASCORBIC ACID DERIVATIVES

(75) Inventors: Thomas Rudolph, Darmstadt (DE); Philipp Buehle, Zwingenberg (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 13/812,869

(22) PCT Filed: Aug. 5, 2011

(86) PCT No.: PCT/EP2011/003951
§ 371 (c)(1),
(2), (4) Date: Jan. 29, 2013

(87) PCT Pub. No.: WO2012/028245
PCT Pub. Date: Mar. 8, 2012

(65) Prior Publication Data
US 2013/0125317 A1    May 23, 2013

(30) Foreign Application Priority Data
Sep. 4, 2010  (DE) ............ 10 2010 044 381

(51) Int. Cl.
*D06P 1/02* (2006.01)
*C09B 37/00* (2006.01)

(52) U.S. Cl.
USPC .............. 8/466; 8/572; 8/576; 534/683

(58) Field of Classification Search
USPC .............. 8/466, 572, 576; 534/683
See application file for complete search history.

(56) References Cited

U.S. PATENT DOCUMENTS 3,345,356 A * 10/1967 Kmiecik ............... 534/585
3,966,900 A *  6/1976 Hennart et al. ......... 424/40

FOREIGN PATENT DOCUMENTS

JP    2008260900 A    10/2008

OTHER PUBLICATIONS

STIC Search dated Jul. 5, 2013.*
STIC Search dated Aug. 27, 2013.*
International Search Report from PCT/EP2011/003951 mailed on Oct. 19, 2011.
English Translation of Abstract related to cited reference JP2008260900A, (2008).

* cited by examiner

*Primary Examiner* — Eisa Elhilo
(74) *Attorney, Agent, or Firm* — Millen, White, Zelano & Branigan, P.C.

(57) ABSTRACT

The invention relates to specific dye-ascorbic acid derivatives and the use thereof as dyes for the coloring of matrices, such as, for example, skin, hair, nails or textiles, and a process for the preparation thereof, a process for the coloring of matrices, and a composition comprising these dye-ascorbic acid derivatives, and a process for the preparation of these compositions. On use of the specific dye-ascorbic acid derivatives according to the invention, a positive effect on the moisture content of the matrices arises.

20 Claims, No Drawings

DYE-ASCORBIC ACID DERIVATIVES

The invention relates to specific dye-ascorbic acid derivatives of the formula I, as described below, and the use thereof as dye for the colouring of a matrix, such as, for example, skin, hair, nails or textiles, and a process for the preparation thereof. The invention furthermore relates to a process for the colouring of a matrix using at least one specific dye-ascorbic acid derivative. The invention furthermore relates to a composition comprising at least one specific dye-ascorbic acid derivative, and a process for the preparation of a composition of this type.

At present, a multiplicity of direct dyes is known for the colouring of a matrix, such as, for example, skin, hair, nails or textiles. The dyes here associate onto the matrix and/or form covalent chemical bonds to the matrix. This binding of the dye molecules to the matrix can occur in various ways and can give different results with respect to the binding character. The dyes are therefore also distinguished by a different binding ability to the respective matrix.

This very binding ability is often weak in dyes which are common today, meaning that the dye can be washed out rapidly by, for example, sweat or water. Owing to the low binding ability of the dye to the respective matrix, the yield of the dye in the colouring process is, in addition, low and consequently the intensity of the colouring of matrices may be low. On use of, in particular synthetic, dyes, in particular in the human area of application, low tolerance may additionally be present.

Thus, there continues to be a demand for, inter alia, tolerated and in particular skin-tolerated dyes which have good binding ability of the dye molecules to the respective matrix, enabling the respective matrix to be coloured durably.

Accordingly, the present invention is concerned with the problem of indicating improved or at least alternative dyes for the colouring of matrices which are distinguished, in particular, by an improved colouring behaviour and which have a positive effect on the moisture content of the matrix, which, in the case of application to hair, results in increased hair elasticity.

This problem is solved in accordance with the invention by the subjectmatters of the independent claims. Advantageous embodiments are the subject-matter of the dependent claims.

Surprisingly, it has now been found that specific dye-ascorbic acid derivatives, in particular the compounds of the formula I, are highly suitable for the colouring of matrices. The ascorbic acid or dehydroascorbic acid may be present in the respective dye-ascorbic acid derivative in the L form or D form or in a mixture of the two isomeric forms. The ascorbic acid or dehydroascorbic acid in the respective dye-ascorbic acid derivative is preferably in the L form.

Hereinbelow, in each case independently of one another:

$Alk^1$ stands for a straight-chain or branched $C_1$- to $C_{20}$-alkyl group or for a straight-chain or branched $C_2$- to $C_{20}$-alkenyl group, which may have a plurality of double bonds, where at least one C atom or a plurality of non-adjacent C atoms of the $C_1$- to $C_{20}$-alkyl or $C_2$- to $C_{20}$-alkenyl group may be replaced by O, where the $C_1$- to $C_{20}$-alkyl or $C_2$- to $C_{20}$-alkenyl group may have at least one OH, F, Cl, Br or I bonded to a primary or secondary C atom;

$Alk^2$ stands for a straight-chain or branched $C_1$- to $C_{20}$-alkyl group;

$Alk^3$ stands for a straight-chain or branched $C_1$- to $C_8$-alkyl group;

Cyc stands for a $C_3$- to $C_8$-cycloalkyl group, which may have at least one double bond, and/or in which at least one $CH_2$ may be replaced by O or NH;

Arl stands for an unsubstituted, mono- or polysubstituted $C_6$- to $C_{20}$-aryl group, where the substituents include OH, $N(Alk^1)_2$, $N(Alk^1)_3An^-$, $Alk^1$, $OAlk^1$, phenyl, biphenyl, naphthyl and anthryl;

a $C_1$-$C_4$-alkyl group here includes methyl, ethyl, propyl-, isopropyl, butyl, x-methylpropyl (x=1;2) and tert-butyl;

a $C_1$-$C_8$-alkyl group here includes the substituents of the $C_1$-$C_4$-alkyl group and pentyl, hexyl, heptyl, octyl, x-methylbutyl (x=1;2;3), x-methylpentyl (x=1;2;3;4), x-methylhexyl (x=1;2;3;4;5), x-ethylpentyl (x=1;2;3) and x-ethylhexyl (x=1;2;3;4);

a $C_1$-$C_{20}$-alkyl group here includes the substituents of the $C_1$-$C_8$-alkyl group and nonanyl, decanyl, undecanyl, dodecanyl, tridecanyl, tetradecanyl, pentadecanyl, hexadecanyl, heptadecanyl, octadecanyl, nonadecanyl and eicosanyl;

a $C_2$-$C_4$-alkenyl group here includes ethenyl, x-propenyl (x=1;2), x-butenyl (x=1;2;3) and butadienyl;

a $C_2$-$C_8$-alkenyl group here includes the substituents of the $C_2$-$C_4$-alkenyl group and x-pentenyl (x=1;2;3;4), x-hexenyl (x=1;2;3;4;5), x-heptenyl (x=1;2;3;4;5;6) and x-octenyl (x=1;2;3;4;5;6;7);

a $C_2$-$C_{20}$-alkenyl group here includes the substituents of the $C_2$-$C_{12}$-alkenyl group and x-nonenyl (x=1;2;3;4;5;6;7;8), x-decenyl (x=1;2;3;4;5;6;7;8;9), x-undecenyl (x=1;2;3;4;5;6;7;8;9;10), x-dodecenyl (x=1;2;3;4;5;6;7;8;9;10;11), 9-octadecenyl, 9,12-octadecadienyl, 9,12,15-octadecatrienyl, 10-nonadecenyl, 10,13-nonadecadienyl, 10,13,16-nonadecatrienyl, 11-eicosenyl, 11,14-eicosadienyl and 11,14,17-eicosatrienyl;

a $C_5$-$C_6$-cycloalkyl group here includes cyclopentyl, x-cyclopentenyl (x=1;2;3), x,y-cyclopentadeinyl (x,y=1,3;1,4;2,4), cyclohexyl, x-cyclohexenyl (x=1;2;3), x,y-cyclohexadienyl (x,y=1,3;1,4;2,4;2,5), x-tetrahydrofuranyl (x=2;3), x-(2,5-dihydrofuranyl) (x=2;3), x-tetrahydropyrrolyl (x=1;2;3), x-(2,5-dihydropyrrolyl) (x=1;2;3), x-(4,5-dihydrooxazolyl) (x=2;4;5), x-oxazolidinyl (x=2;3;4;5), x-piperidinyl (x=2;3;4;5), x-pyranyl (x=2;3;4;5), x-(4,5-dihydropyranyl) (x=2;3;4;5), x-piperazinyl (x=2;3), x-(1,3-dioxanyl) (x=2;4;5;6) and x-(1,4-dioxanyl) (x=2;3;5;6), x-(tetrahydro-1,2-oxazinyl) (x=2;3;4;5;6), x-(tetrahydro-1,3-oxazinyl) (x=2;3;4;5;6) and x-(tetrahydro-1,4-oxazinyl) (x=2;3;4;5;6);

a $C_3$-$C_8$-cycloalkyl group here includes the substituents of the $C_5$-$C_6$-cycloalkyl group and cyclopropyl, x-cyclopropenyl (x=1;2), cyclobutanyl, x-cyclobutenyl (x=1;2;3), cycloheptyl, cyclooctyl, x-methylcylclohexyl (x=2;3;4), x-ethylcyclohexyl (x=2;3;4) and x,y-dimethylcyclohexyl (x,y=2,3;2,4);

a $C_6$-$C_{12}$-aryl group here includes phenyl, naphthyl and biphenylyl, a $C_6$-$C_{15}$-aryl group here includes the substituents of the $C_6$-$C_{12}$-aryl group and anthryl, and phenanthryl;

a $C_6$-$C_{20}$-aryl group here includes the substituents of the $C_6$-$C_{15}$-aryl group and pyrenyl, chrysenyl naphthacenyl and picenyl;

a mono- or polysubstituted $C_6$-$C_{12}$-aryl group here includes x-methylphenyl (x=o,m,p), x-ethylphenyl (x=o,m,p), x-propylphenyl (x=o,m,p), x-isopropylphenyl (x=o,m,p), x-tert-butylphenyl (x=o,m,p), x-nitrophenyl (x=o,m,p), x-methoxyphenyl (x=o,m,p), x-ethoxyphenyl (x=o,m,p), (x=o,m,p), x,ydimethylphenyl (x=2,3;2,4;2,5;2,6;3,4;3,5), x,y-dihydroxyphenyl (x=2,3;2,4;2,5;2,6;3,4;3,5), x,y-dimethoxyphenyl (x=2,3;2,4;2,5;2,6;3,4;3,5), 3,4,5-trimethoxyphenyl and 2,4,5-trimethylphenyl, where OH, $N(Alk^1)_2$, $N(Alk^1)_3An^-$, $Alk^1$, $OAlk^1$, phenyl, biphenyl, naphthyl and anthryl may occur as further substituents;

a mono- or polysubstituted $C_6$-$C_{15}$-aryl group here includes the substituents of the mono- or polysubstituted $C_6$-$C_{12}$-aryl group;

a mono- or polysubstituted $C_6$-$C_{20}$-aryl group here includes the substituents of the mono- or polysubstituted $C_6$-$C_{15}$-aryl group.

The invention thus relates to compounds of the formula I

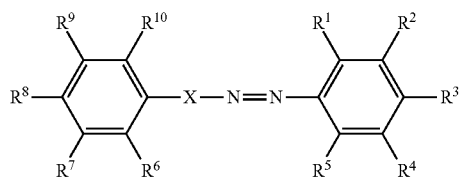

I where X stands for a single bond or a substituent of the formula IIa or IIb

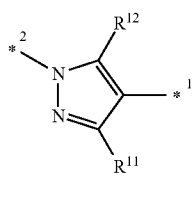

IIa

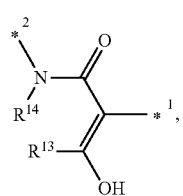

IIb where *¹ is oriented towards the N═N, where precisely one of the substituents $R^1$ to $R^{14}$ stands for a substituent of the formula IIIa, IIIb or IIIc

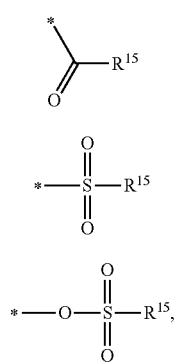

IIIa

IIIb

IIIc where $R^{15}$ in each case stands, independently of one another, for an ascorbic acid radical of the formula IVa or IVb or a dehydroascorbic acid radical of the formula IVc or IVd

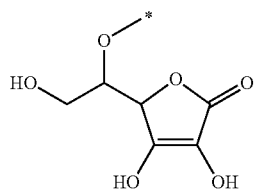

IVa

IVb

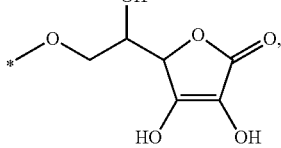

IVc

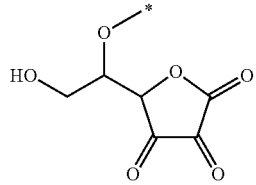

IVd where the remaining substituents $R^1$ to $R^{14}$ each stand, independently of one another, for H, OH, $NH_2$, $NO_2$, F, Cl, Br, I, $CF_3$, $OCF_3$, O(C═O)—$CH_2$—$NH_2$, $Alk^1$, $OAlk^1$, $NHAlk^1$, $NAlk^1_2$, Cyc, $(NAlk^1_3)^+_x An^{x-}$, $(SO_2)NH_2$, $(SO_2)NHAlk^1$, $O(SO_2)OAlk^1$, $O(SO_2)OArl$, (C═O)$OAlk^1$, (C═O)$OArl$ or Arl, where $Alk^1$ in each case stands, independently of one another, for a straight-chain or branched $C_1$- to $C_{20}$-alkyl group or for a straight-chain or branched $C_2$- to $C_{20}$-alkenyl group, which may have a plurality of double bonds, where at least one C atom or a plurality of non-adjacent C atoms of the $C_1$- to $C_{20}$-alkyl or $C_2$- to $C_{20}$-alkenyl group may be replaced by O, where the $C_1$- to $C_{20}$-alkyl or $C_2$- to $C_{20}$-alkenyl group may have at least one OH, F, Cl, Br or I bonded to a primary or secondary C atom, where Arl in each case stands, independently of one another, for an unsubstituted, mono- or polysubstituted $C_6$- to $C_{20}$-aryl group, where Cyc stands for a $C_3$- to $C_8$-cycloalkyl group, which may have at least one double bond and/or in which at least one $CH_2$ may be replaced by O or NH, where $An^{x-}$ in each case stands, independently of one another, for an anion having the charge 1≤x≤3 and/or tautomers, stereoisomers thereof, including mixtures thereof in all ratios.

Suitable as anion $An^{x-}$ are all anions which are tolerated for a cosmetic application. Illustrative anions are anions of the physiologically acceptable acids from the group sulfuric acid, sulfurous acid, dithionic acid, nitric acid, hydrohalic acids, such as hydrochloric acid or hydrobromic acid, phosphoric acids, such as, for example, orthophosphoric acid, sulfamic acid, furthermore organic acids, in particular aliphatic, alicyclic, araliphatic, aromatic or heterocyclic mono- or polybasic carboxylic, sulfonic or sulfuric acids, for example formic acid, acetic acid, propionic acid, hexanoic acid, octanoic acid, decanoic acid, hexadecanoic acid, octadecanoic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, benzenesulfonic acid, trimethoxybenzoic acid, adamantanecarboxylic acid, p-toluenesulfonic acid, glycolic acid, embonic acid, chlorophenoxyacetic acid, aspartic acid, glutamic acid, proline, glyoxylic acid, palmitic acid, parachlorophenoxyisobutyric acid, cyclohexanecarboxylic acid, glucose 1-phosphate, naphthalenemono- and disulfonic acids or laurylsulfuric acid.

A compound of the formula I containing at least one functionality $N(Alk^1)_2$ can be converted into the associated acid-addition salt containing the $N(Alk^1)_3An^{x-}$ group using an acid, for example by reaction of equivalent amounts of this compound of the formula I and the acid in an inert solvent, such as ethanol, and subsequent evaporation. The acid is selected as described above.

Through derivatisation of specific azo compounds of the formula V, as described below, with ascorbic acid or dehydroascorbic acid, the colouring behaviour of such compounds of the formula I is, surprisingly, significantly improved compared with the azo compounds of the formula V themselves.

Dehydroascorbic acid of the formula IX represents an oxidised form of ascorbic acid of the formula VIII which can be reduced back to ascorbic acid in the human organism.

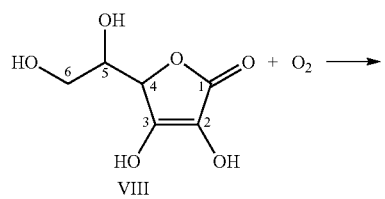

VIII

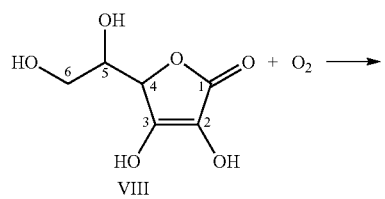

IX

The numbering of positions of ascorbic acid of the formula VIII and of dehydroascorbic acid of the formula IX is as depicted in the above reaction scheme.

Since azo compounds have azo-hydrazo tautomerism and to a predetermined percentage exist both in the azo form and in the hydrazo form under corresponding ambient conditions, a compound of the formula I is for the purposes of the invention taken to mean the azo form shown in the formula I and also the hydrazo form, which is not depicted.

Preference is given to compounds of the formula I in which $R^{15}$ in each case stands, independently of one another, for an L-ascorbic acid radical of the formula IVa-1 or IVb-1 or an L-dehydroascorbic acid radical of the formula IVc-1 or IVd-1.

Preferred compounds of the formula I are therefore compounds of the formula I

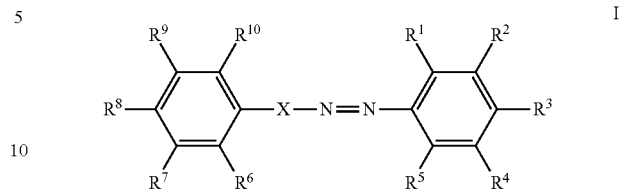

I where X stands for a single bond or a substituent of the formula IIa or IIb

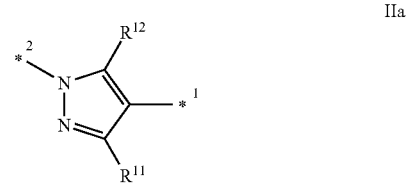

IIa

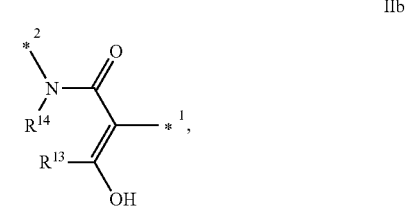

IIb where $*^1$ is oriented towards the N=N,
where precisely one of the substituents $R^1$ to $R^{14}$ stands for a substituent of the formula IIIa, IIIb or IIIc

IIIa

IIIb

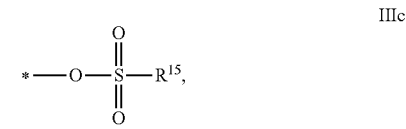

IIIc where $R^{15}$ in each case stands, independently of one another, for an L-ascorbic acid radical of the formula IVa-1 or IVb-1 or a dehydroascorbic acid radical of the formula IVc-1 or IVd-1

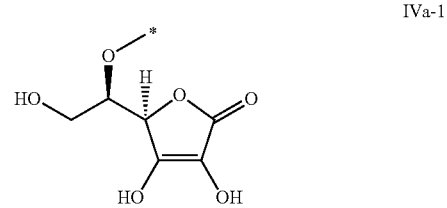

IVa-1

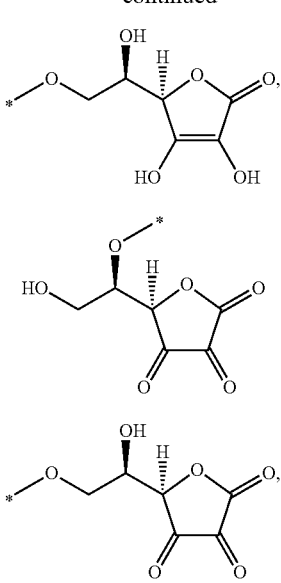

where the remaining substituents $R^1$ to $R^{14}$ each stand, independently of one another, for H, OH, $NH_2$, $NO_2$, F, Cl, Br, I, $CF_3$, $OCF_3$, O(C=O)—$CH_2$—$NH_2$, $Alk^1$, $OAlk^1$, $NHAlk^1$, $NAlk^1{}_2$, Cyc, $(NAlk^1{}_3)^+{}_x An^{x-}$, $(SO_2)NH_2$, $(SO_2)NHAlk^1$, $O(SO_2)OAlk^1$, $O(SO_2)OArl$, (C=O)$OAlk^1$, (C=O)OArl or Arl, where $Alk^1$ in each case stands, independently of one another,
for a straight-chain or branched $C_1$- to $C_{20}$-alkyl group or for a straight-chain or branched $C_2$- to $C_{20}$-alkenyl group, which may have a plurality of double bonds, where at least one C atom or a plurality of non-adjacent C atoms of the $C_1$- to $C_{20}$-alkyl or $C_2$- to $C_{20}$-alkenyl group may be replaced by O, where the $C_1$- to $C_{20}$-alkyl or $C_2$- to $C_{20}$-alkenyl group may have at least one OH, F, Cl, Br or I bonded to a primary or secondary C atom, where Arl in each case stands, independently of one another, for an unsubstituted, mono- or polysubstituted $C_6$- to $C_{20}$-aryl group, where Cyc stands for a $C_3$- to $C_8$-cycloalkyl group, which may have at least one double bond and/or in which at least one $CH_2$ may be replaced by O or NH, where $An^{x-}$ in each case stands, independently of one another, for an anion having the charge $1 \leq x \leq 3$.

Preference is given to compounds of the formula I in which the remaining substituents $R^1$ to $R^{14}$ each stand, independently of one another, for H, OH, $NH_2$, $NO_2$, F, Cl, Br, I, $CF_3$, $OCF_3$, $Alk^1$, $OAlk^1$, $NHAlk^1$, $NAlk^1{}_2$, $(NAlk^1{}_3)^+{}_x An^{x-}$, $(SO_2)NH_2$, $(SO_2)NHAlk^1$, (C=O)$OAlk^1$, (C=O)OArl or Arl.

Particular preference is given to compounds of the formula I in which the remaining substituents $R^1$ to $R^{14}$ each stand, independently of one another, for H, OH, $N(Alk^1)_2$, $Alk^1$, $N(Alk^1)_3 Arl$ or Arl.

It is preferred if at least one of the remaining substituents $R^1$ to $R^{14}$ stands for OH, $Alk^1$, $N(Alk^1)_2$, $(NAlk^1{}_3)^+{}_x An^{x-}$ or Arl and the other remaining substituents stand for H.

Very particular preference is given to compounds of the formula I in which the remaining substituents $R^1$ to $R^{10}$ stand for H or $N(Alk^1)_2$. It is very particularly preferred if at least one of the remaining substituents $R^1$ to $R^{10}$ stands for $N(Alk^1)_2$ and the other remaining substituents stand for H. It is preferred here if precisely one remaining substituent $R^1$ to $R^{10}$ stands for $N(Alk^1)_2$ and the other remaining substituents stand for H.

In the definitions described above for the remaining substituents $R^1$ to $R^{14}$, $Alk^1$ can preferably stand for $Alk^2$ and particularly preferably for $Alk^3$.

$R^{11}$ and $R^{12}$ preferably each stand, independently of one another, for OH or for $Alk^3$. Very particularly preferably, one substituent $R^{11}$ or $R^{12}$ stands for OH and the other substituent stands for H.

A remaining substituent $R^1$ to $R^{14}$ here is taken to mean the substituents $R^1$ to $R^{14}$ which are not substituted by a substituent of the formula IIIa, IIIb or IIIc.

Preference is given to compounds in which at least 2 of the $R^1$ to $R^5$ stand for H, particularly preferably compounds in which at least 3 of the $R^1$ to $R^5$ stand for H and very particularly preferably compounds in which at least 4 of the $R^1$ to $R^5$ stand for H, where the other substituents $R^1$ to $R^5$ have the meaning of the remaining substituents $R^1$ to $R^5$ described above.

Preference is given to compounds in which at least 2 substituents of the substituents $R^6$ to $R^{10}$ stand for H, particular preference is given to compounds in which at least 3 substituents of the substituents $R^6$ to $R^{10}$ stand for H and very particular preference is given to compounds in which at least 4 substituents of the substituents $R^6$ to $R^{10}$ stand for H, where the other substituents $R^6$ to $R^{10}$ have the meaning of the remaining substituents $R^6$ to $R^{10}$ described above.

An other substituent $R^1$ to $R^{10}$ here is taken to mean the substituents $R^1$ to $R^{10}$ which are not substituted by a substituent of the formula IIIa, IIIb or IIIc or which are not H.

Preference is given to compounds containing a substituent of the formula IIa for X or containing a single bond for X.

Particular preference is given to compounds in which precisely one of the substituents $R^1$ to $R^5$ or precisely one of the substituents $R^6$ to $R^{10}$ stands for a substituent of the formula IIIa, IIIb or IIIc.

Preference is given to compounds in which precisely one of the substituents $R^1$ to $R^5$ or precisely one of the substituents $R^6$ to $R^{10}$ stands for a substituent of the formula IIIa or IIIb.

$R^{15}$ stands for an ascorbic acid radical of the formula IVa or IVb or a dehydroascorbic acid radical of the formula IVc or IVd, where the ascorbic acid may be in the D or L form or in the form of a mixture, in particular not equimolar, of the two enantiomeric forms.

$R^{15}$ preferably stands for an ascorbic acid radical of the formula IVa-1 or IVb-1, as described above.

Particular preference is given to the 6-0 ester of ascorbic acid, and $R^{15}$ thus particularly preferably stands for an ascorbic acid radical of the formula IVb, where the ascorbic acid may be in the D or L form or in the form of a mixture, in particular not equimolar, of the two enantiomeric forms.

$R^{15}$ very particularly preferably stands for an L-ascorbic acid radical of the formula IVb-1.

Particularly preferred compounds of the formula I are
(R)-2-((R)-3,4-dihydroxy-5-oxo-2,5-dihydrofuran-2-yl)-2-hydroxyethyl 4-phenylazobenzoate,
(R)-2-((R)-3,4-dihydroxy-5-oxo-2,5-dihydrofuran-2-yl)-2-hydroxyethyl 4-(4-dimethylaminophenylazo)benzoate,
2-(R)-((R)-(3,4-dihydroxy-5-oxo-2,5-dihydrofuran-2-yl)-2-hydroxyethyl 4-(4-dimethylaminophenylazo)phenylsulfonate or
(R)-2-((R)-3,4-dihydroxy-5-oxo-2,5-dihydrofuran-2-yl)-2-hydroxyethyl 2-(5-hydroxy-3-methyl-1-phenyl-1H-pyrazol-4-ylazo)benzoate.

A very particularly preferred compound of the formula I is (R)-2-((R)-3,4-dihydroxy-5-oxo-2,5-dihydrofuran-2-yl)-2-hydroxyethyl 4-phenylazobenzoate.

Compounds of the formula I thus have precisely one ascorbic acid radical of the formula IVa, IVb, IVa-1 or IVb-1 or dehydroascorbic acid radical of the formula IVc, IVd, IVc-1 or IVd-1 as linker and a radical of an azo compound of the formula V, as described below. The linker ascorbic acid or the linker dehydroascorbic acid improves the binding ability of the compounds of the formula I, since the compound of the formula I also associates onto the respective matrix and/or a covalent bond can be formed to the respective matrix by means of the respective linker. For this reason, inter alia, the compounds of the formula I have significantly improved binding ability compared with azo compounds of the formula V described below, with the result that colouring of matrices using compounds of the formula I is distinguished by pronounced durability of the colouring, in particular to washing out.

Furthermore, these linkers represent natural linkers which are advantageously tolerated, in particular by humans. Thus, the compounds of the formula I are generally likewise tolerated better, in particular by humans.

Surprisingly, more intense colouring can additionally be achieved with compounds of the formula I. For this reason, inter alia, the yield in the colouring process is increased, since more intense colouring can be achieved at the same molar use concentration than with the azo compounds of the formula V described below. Matrices which are coloured with compounds of the formula I are accordingly distinguished by more intense colouring. Costs, both during the colouring process and also with respect to requisite repetition of the colouring, can thus advantageously be significantly reduced.

In addition, the compounds of the formula I are colour-stable and photostable. They are additionally distinguished by improved biological degradabilities and are thus more environmentally friendly.

For example, a compound A containing two ascorbic acid radicals exhibits a lower dipole moment than a compound B having only one ascorbic acid radical. The dipole moments are indicated in brackets after the compound.

compound A

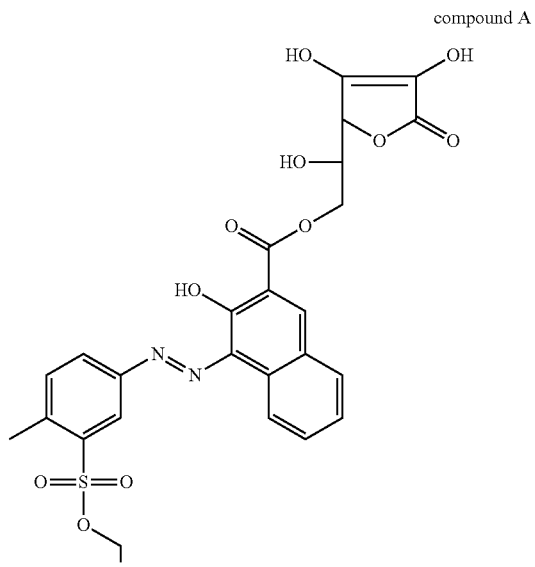

(4.1491)

compound B

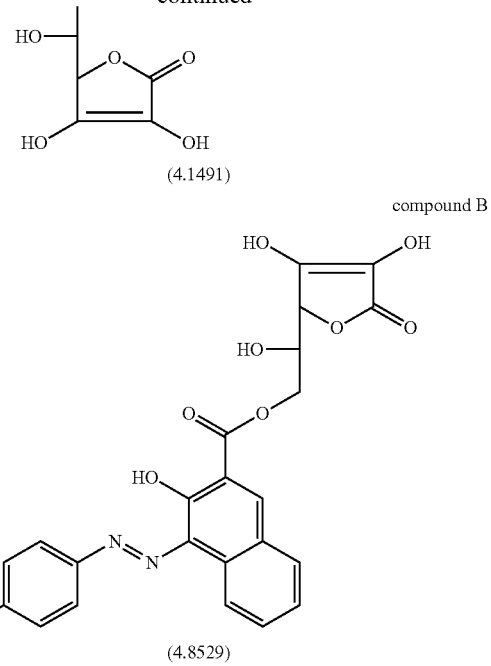

(4.8529)

The dipole moments of the two compounds A and B were determined here by means of the Gaussian 03W software from Gaussian Inc. quantum simulations. To this end, the molecular geometry was optimised by means of the semi-empirical quantum-chemical method AM ("Austin Model 1"), and the TD-DFT (time dependent density function theory) was then applied, where the calculations for the dipole moments were carried out by means of the density functional theory method B3PW91 and the function base set 6-31G(d) (relative units). A dipole moment for compound B which is, at 4.8529, significantly higher than for compound A, whose dipole moment is 4.1491, is determined in this way.

The compounds of the formula I, as described above, are thus advantageously improved compared with compounds having a plurality of ascorbic acid radicals, at least with respect to their higher dipole moment which arises, so that compounds of the formula I may have improved amphiphilicity compared with compounds having more than one ascorbic acid radical.

Through the use of precisely one ascorbic acid radical of the formula IVa, IVb, IVa-1 or IVb-1 or dehydroascorbic acid radical of the formula IVc, IVd, IVc-1 or IVd-1 as linker, compounds of the formula I may thus be more amphiphilic, which is why the penetration of the compounds of the formula I into the matrix takes place more easily. For this reason, inter alia, more complete and longer-lasting colouring can be achieved, meaning that, also owing to the depth action of the compounds of the formula I, colouring with compounds of the formula I, as described above or described as preferred, has a higher yield.

In addition, owing to the high amphiphilicity and the high water-binding capacity of the compounds of the formula I, the moisture content of a matrix treated with at least one compound of the formula I is significantly improved. This results in improved matrix structure properties and in increased elasticity of the matrix.

Based on the preferred matrix hair, the following statements, in particular, apply: the compounds of the formula I and the compounds of the formula I indicated as preferred, colour hair more intensely compared with the dye without ascorbic acid linkers. The compounds of the formula I and the compounds of the formula I indicated as preferred are suitable for penetrating through the hair cuticles into the hair cortex, enabling complete and lasting hair colouring to be achieved over the entire hair. Furthermore, the compounds of the formula I and the compounds of the formula I indicated as preferred improve the hair moisture content due to excellent hydration of the hair keratin. The hair structure properties, in particular the hair elasticity, thus improve in association with the hair moisture content.

The invention furthermore relates to a process for the preparation of a compound of the formula I, as described above, in which, in an esterification step, precisely one acid group of the formula VIIa, VIIb or VIIc of an azo compound of the formula V,

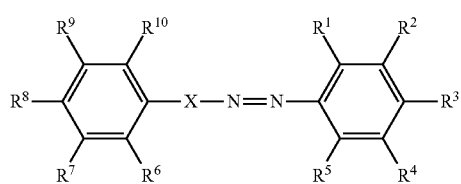

where X stands for a single bond or a substituent of the formula VIa or VIb

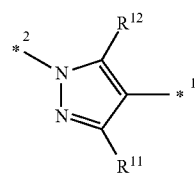

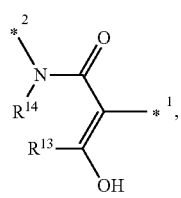

where *$^1$ is oriented towards the N=N, where precisely one of the substituents $R^1$ to $R^{14}$ in each case stands, independently of one another, for an acid group of the formula VIIa, VIIb or VIIc

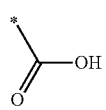

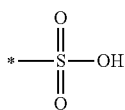

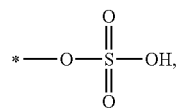

where the remaining substituents $R^1$ to $R^{14}$ have a meaning described above, is reacted with precisely one hydroxyl group in the fifth or sixth position of the ascorbic acid or dehydroascorbic acid.

The linker ascorbic acid, preferably L-ascorbic acid, or dehydroascorbic acid, preferably L-dehydroascorbic acid, is thus bonded to the azo compound of the formula V by esterification via one of its OH groups in the fifth and/or sixth position. Suitable in accordance with the invention are therefore azo compounds of the formula V which have precisely one carboxyl, sulfonyl or HO(SO$_2$)O group or salts or activated forms thereof, such as, for example, active esters, acid chlorides or the like.

Before the esterification step, the acid group of the formula VIIa, VIIb or VIIc of the respective azo compound of the formula V can be activated for a subsequent esterification in an activation step. For this purpose, an active ester, an acid chloride or the like can be prepared from the azo compound of the formula V.

Furthermore, before the esterification step and, where appropriate, before the activation step, at least one hydroxyl group in the fifth or sixth position of the ascorbic acid or dehydroascorbic acid can be protected by means of a first protecting group. Likewise, at least one hydroxyl group in the second or third position of the ascorbic acid can furthermore be protected by a second protecting group.

After the esterification step, at least one first and/or second protecting group can be cleaved off, where the first and second protecting groups can be cleaved off under different reaction conditions.

Protecting groups which can be employed are the usually known and frequently used protecting groups, such as, for example, methoxymethyl, benzyl, silyl groups or the like.

A further core idea of the invention is the use of compounds of the formula I, as described above, as dye for a matrix, in particular a protein-containing matrix.

Matrix here is taken to mean a polymeric compound which has, as functional group, at least one free NH, NH$_2$, SH or OH groups. Inter alia owing to the functional groups of the matrix, the dye derivative is capable of associating onto the matrix and, where appropriate, forming a covalent bond with the matrix. Preferred matrices here are protein-containing matrices. Particular preference is given to skin, hair and/or nails and very particular preference is given to hair. Likewise suitable are matrices such as, for example, isolated proteins or gelatine. Furthermore, synthetic polymeric compounds which has at least one of the above-mentioned functional groups are likewise suitable. Accordingly, the compounds of the formula I can also be used for the colouring of textiles, including plastic fibres, or very generally of plastics. In particular, fibres containing wool, cotton or silk can be used for textile colouring.

Preferably, at least two compounds of the formula I are used, where the compounds differ with respect to $R^{15}$ and $R^{15}$ stands for an ascorbic acid radical of the formula IVa or IVb or for a dehydroascorbic acid radical of the formula IVc or IVd, in each case as the L or D enantiomer, or preferably for an ascorbic acid radical of the formula IVa-1 or IVb-1 or a dehydroascorbic acid radical of the formula IVc-1 or IVd-1.

L/D mixtures of this type can be prepared by esterification of an azo compound of the formula V using a racemic, in particular non-equimolar mixture of L- and D-ascorbic acid and/or L- and D-dehydroascorbic acid, preferably using L-ascorbic acid.

A further inventive idea is a process for the colouring of a matrix, in particular a protein-containing matrix, in which the matrix is coloured directly, in a colouring step, by the action of a dispersion and/or solution and/or emulsion of a compound of the formula I, as described above, on the matrix.

In a pretreatment step, the matrix can be pretreated by means of a pretreatment agent in order to influence and in particular to improve the colouring behaviour. A pretreatment agent of this type may be basic, acidic or neutral, have an oxidative action, for example through the presence of an oxidant, such as hydrogen peroxide, and optionally comprise water. The pretreatment step is usually carried out before the colouring step.

At the same time, compounds of the formula I are very good antioxidants owing to their ascorbic acid origin. This is advantageous, since colouring procedures, in particular hair-colouring processes, proceed under conditions, for example alkaline conditions, in the presence of oxidants, such as hydrogen peroxide and/or ammonium peroxide, which result in the formation of reactive oxygen and/or nitrogen and/or carbon species (for example ROS reactive oxygen species). These can damage adhering fabric such as wool, skin or hair. Antioxidants counter this effect.

The invention furthermore relates to compositions which comprise at least one compound of the formula I, as described above. These compositions may furthermore comprise at least one vehicle which is suitable for cosmetic, pharmaceutical, dermatological compositions or household products.

In preferred embodiments, the at least one compound of the formula I containing the substituents defined or indicated as preferred is typically employed in the compositions according to the invention in amounts of 0.05 to 10% by weight, preferably in amounts of 0.1% by weight to 5% by weight and particularly preferably in amounts of 0.5 to 2% by weight.

The invention furthermore relates to a process for the preparation of a composition of this type, as described above, in which at least one compound of the formula I is mixed, in particular dispersed and/or emulsified and/or dissolved, with at least one vehicle which is suitable for cosmetic, pharmaceutical, dermatological compositions or household products and optionally assistants and/or fillers. Suitable vehicles and active substances or assistants are described in detail in the following part.

The compositions here are usually compositions for application to textiles or for application to human and animal skin and hair. Cosmetic or dermatological formulations or medical devices are examples. In this case, the compositions comprise a cosmetically or dermatologically suitable vehicle and, depending on the desired property profile, optionally further suitable ingredients. In the case of pharmaceutical compositions, the compositions in this case comprise a pharmaceutically tolerated vehicle and optionally further pharmaceutical active compounds.

"Can be applied topically" in the sense of the invention means that the composition is applied externally and locally, i.e. that the composition must be suitable for, for example, application to the skin.

In the sense of the present invention, the term agent or formulation is also used synonymously alongside the term composition.

The compositions may include or comprise, essentially consist of or consist of the said requisite or optional constituents. All compounds or components which can be used in the compositions are either known and commercially available or can be synthesised by known processes.

Further preferred combinations of embodiments are disclosed in the claims.

The compositions described which, in accordance with the invention, comprise at least one compound of the formula I, may furthermore also comprise coloured pigments, where the layer structure of the pigments is not limited.

The coloured pigment should preferably be skin-coloured or brownish on use of 0.5 to 5% by weight. The choice of a corresponding pigment is familiar to the person skilled in the art.

Besides the compounds of the formula I, preferred compositions may comprise organic UV filters, so-called hydrophilic or lipophilic sun-protection filters, which are effective in the UVA region and/or UVB region and(/or IR and/or VIS region (absorbers). These substances may be selected, in particular, from cinnamic acid derivatives, salicylic acid derivatives, camphor derivatives, triazine derivatives, β,β-diphenylacrylate derivatives, p-aminobenzoic acid derivatives and polymeric filters and silicone filters, which are described in the application WO-93/04665. Further examples of organic and also inorganic UV filters are indicated in the patent applications EP-A 0 487 404 and WO2009/077356. The said UV filters are usually named below in accordance with INCI nomenclature.

Particularly suitable for a combination are:

para-aminobenzoic acid and derivatives thereof: PABA, Ethyl PABA, Ethyl dihydroxypropyl PABA, Ethylhexyl dimethyl PABA, for example marketed by ISP under the name "Escalol 507", Glyceryl PABA, PEG-25 PABA, for example marketed by BASF under the name "Uvinul P25".

Salicylates: Homosalate marketed by Merck under the name "Eusolex HMS"; Ethylhexyl salicylate, for example marketed by Symrise under the name "Neo Heliopan OS", Dipropylene glycol salicylate, for example marketed by Scher under the name "Dipsal", TEA salicylate, for example marketed by Symrise under the name "Neo Heliopan TS".

β,β-Diphenylacrylate derivatives: Octocrylene, for example marketed by Merck under the name "Eusolex® OCR", by BASF under the name "Uvinul N539", Etocrylene, for example marketed by BASF under the name "Uvinul N35".

Benzophenone derivatives: Benzophenone-1, for example marketed under the name "Uvinul 400"; Benzophenone-2, for example marketed under the name "Uvinul D50"; Benzophenone-3 or Oxybenzone, for example marketed under the name "Uvinul M40";Benzophenone-4, for example marketed under the name "Uvinul MS40"; Benzophenone-9, for example marketed by BASF under the name "Uvinul DS-49", Benzophenone-5, Benzophenone-6, for example marketed by Norquay under the name "Helisorb 11", Benzophenone-8, for example marketed by American Cyanamid under the name "Spectra-Sorb UV-24", Benzophenone-12 n-hexyl 2-(4-diethylamino-2-hydroxybenzoyl)benzoate or 2-hydroxy-4-methoxybenzophenone, marketed by Merck, Darmstadt, under the name Eusolex® 4360.

Benzylidenecamphor derivatives: 3-Benzylidenecamphor, for example marketed by Chimex under the name "Mexoryl SD", 4-Methylbenzylidenecamphor, for example marketed by Merck under the name "Eusolex 6300", benzylidenecamphorsulfonic acid, for example marketed by Chimex under the name "Mexoryl SL", Camphor benzalkonium methosulfate, for example marketed by Chimex under the name "Mexoryl SO", terephthalylidenedicamphorsulfonic acid, for example marketed by Chimex under the name "Mexoryl SX", Polyacrylamidomethylbenzylidenecamphor marketed by Chimex under the name "Mexoryl SW".

Phenylbenzimidazole derivatives: phenylbenzimidazolesulfonic acid, for example marketed by Merck under the name "Eusolex 232", disodium phenyl dibenzimidazole tetrasulfonate, for example marketed by Symrise under the name "Neo Heliopan AP".

Phenylbenzotriazole derivatives: Drometrizole trisiloxane, for example marketed by Rhodia Chimie under the name "Silatrizole", Methylenebis(benzotriazolyl)tetramethylbutylphenol in solid form, for example marketed by Fairmount Chemical under the name "MIXXIM BB/100", or in micronised form as an aqueous dispersion, for example marketed by BASF under the name "Tinosorb M".

Triazine derivatives: Ethylhexyltriazone, for example marketed by BASF under the name "Uvinul T150", Diethylhexylbutamidotriazone, for example marketed by Sigma 3V under the name "Uvasorb HEB", 2,4,6-tris(diisobutyl 4'-aminobenzalmalonate)-s-triazine or 2,4,6-Tris-(biphenyl)-1,3,5-triazine.

Anthraniline derivatives: Menthyl anthranilate, for example marketed by Symrise under the name "Neo Heliopan MA".

Imidazole derivatives: Ethylhexyldimethoxybenzylidenedioxoimidazoline propionate.

Benzalmalonate derivatives: polyorganosiloxanes containing functional benzalmalonate groups, such as, for example, polysilicone-15, for example marketed by Hoffmann LaRoche under the name "Parsol SLX".

4,4-Diarylbutadiene derivatives: 1,1-Dicarboxy(2,2'-dimethylpropyl)-4,4-diphenylbutadiene.

Benzoxazole derivatives: 2,4-bis[5-(1-dimethylpropyl)benzoxazol-2-yl(4-phenyl) imino]-6-(2-ethylhexyl)imino-1,3,5-triazine, for example marketed by Sigma 3V under the name Uvasorb K2A, and mixtures comprising this.

Piperazine derivatives, such as, for example, the compound

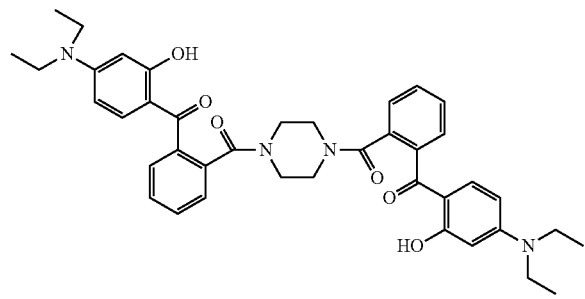 [SMILES: CCN(CC)c1ccc(C(=O)c2ccccc2C(=O)N2CCN(C(=O)c3ccccc3C(=O)c3ccc(N(CC)CC)cc3O)CC2)c(O)c1]

or the UV filters of the following structures:

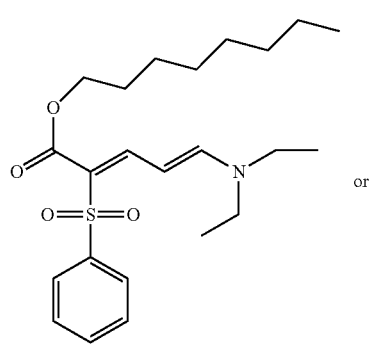

or

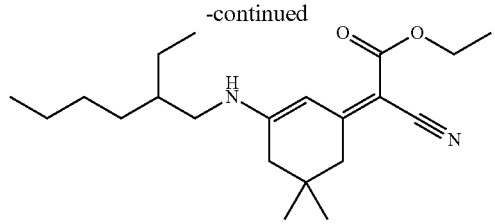

It is also possible to use UV filters based on polysiloxane copolymers having a random distribution in accordance with the following formula, where, for example, $a=1.2$; $b=58$ and $c=2.8$:

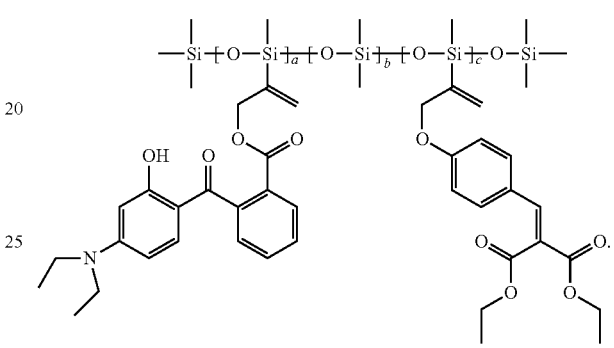

The compounds listed should only be regarded as examples. It is of course also possible to use other UV filters.

Suitable organic UV-protecting substances can preferably be selected from the following list: Ethylhexyl salicylate, Phenylbenzimidazolesulfonic acid, Benzophenone-3, Benzophenone-4, Benzophenone-5, n-Hexyl 2-(4-diethylamino-2-hydroxybenzoyl)benzoate, 4-Methylbenzylidenecamphor, Terephthalylidenedicamphorsulfonic acid, Disodium phenyldibenzimidazoletetrasulfonate, Methylenebis(benzotriazolyl)tetramethylbutylphenol, Ethylhexyl Triazone, Diethylhexyl Butamido Triazone, Drometrizole trisiloxane, Polysilicone-15, 1,1-Dicarboxy(2,2'-dimethylpropyl)-4,4-diphenylbutadiene, 2,4-Bis[5-1(dimethylpropyl)benzoxazol-2-yl(4-phenyl) imino]-6-(2-ethylhexyl)imino-1,3,5-triazine and mixtures thereof.

These organic UV filters are generally incorporated into formulations in an amount of 0.01 percent by weight to 20 percent by weight, preferably 1% by weight-10% by weight.

Besides the compounds of the formula I and the, where appropriate, other organic UV filters, as described above, preferred compositions may comprise further inorganic UV filters, so-called particulate UV filters.

These combinations with particulate UV filters are possible both as powder and also as dispersion or paste of the following types.

Preference is given here both to those from the group of the titanium dioxides, such as, for example, coated titanium dioxide (for example Eusolex® T-2000, Eusolex®T-AQUA, Eusolex®T-AVO, Eusolex®T-OLEO), zinc oxides (for example Sachtotec®), iron oxides or also cerium oxides and/or zirconium oxides.

Furthermore, combinations with pigmentary titanium dioxide or zinc oxide are also possible, where the particle size of these pigments are greater than or equal to 200 nm, for example Hombitan® FG or Hombitan® FF-Pharma.

It may further be preferred for the compositions to comprise inorganic UV filters which have been aftertreated by conventional methods, as described, for example, in Cosmetics & Toiletries, February 1990, Vol. 105, pp. 53-64. One or more of the following aftertreatment components can be selected here: amino acids, beeswax, fatty acids, fatty acid alcohols, anionic surfactants, lecithin, phospholipids, sodium, potassium, zinc, iron or aluminium salts of fatty acids, polyethylenes, silicones, proteins (particularly collagen or elastin), alkanolamines, silicon dioxide, aluminium oxide, further metal oxides, phosphates, such as sodium hexametaphosphate, or glycerine.

Particulate UV filters which are preferably employed here are:

untreated titanium dioxides, such as, for example, the products Microtitanium Dioxide MT 500 B from Tayca; titanium dioxide P25 from Degussa, Aftertreated micronised titanium dioxides with aluminium oxide and silicon dioxide aftertreatment, such as, for example, the product "Microtitanium Dioxide MT 100 SA from Tayca; or the product "Tioveil Fin" from Uniqema, Aftertreated micronised titanium dioxides with aluminium oxide and/or aluminium stearate/laurate aftertreatment, such as, for example, Microtitanium Dioxide MT 100 T from Tayca, Eusolex T-2000 from Merck, Aftertreated micronised titanium dioxides with iron oxide and/or iron stearate aftertreatment, such as, for example, the product "Microtitanium Dioxide MT 100 F" from Tayca, Aftertreated micronised titanium dioxides with silicon dioxide, aluminium oxide and silicone aftertreatment, such as, for example, the product "Microtitanium Dioxide MT 100 SAS", from Tayca, Aftertreated micronised titanium dioxides with sodium hexametaphosphates, such as, for example, the product "Microtitanium Dioxide MT 150 W" from Tayca.

The treated micronised titanium dioxides employed for the combination may also be aftertreated with:

octyltrimethoxysilanes; such as, for example, the product Tego Sun T 805 from Degussa, silicon dioxide; such as, for example, the product Parsol T-X from DSM, aluminium oxide and stearic acid; such as, for example, the product UV-Titan M160 from Sachtleben, aluminium and glycerine; such as, for example, the product UV-Titan from Sachtleben, aluminium and silicone oils, such as, for example, the product UV-Titan M262 from Sachtleben, sodium hexamethaphosphate and polyvinylpyrrolidone, polydimethylsiloxanes, such as, for example, the product 70250 Cardre UF TiO2SI3" from Cardre, polydimethylhydrogensiloxanes, such as, for example, the product Microtitanium Dioxide USP Grade Hydrophobic" from Color Techniques.

The combination with the following products may furthermore also be advantageous:

Untreated zinc oxides, such as, for example, the product Z-Cote from BASF (Sunsmart), Nanox from Elementis Aftertreated zinc oxides, such as, for example, the following products:

"Zinc Oxide CS-5" from Toshibi (ZnO aftertreated with polymethylhydrogenosiloxanes)

Nanogard Zinc Oxide FN from Nanophase Technologies

"SPD-Z1" from Shin-Etsu (ZnO aftertreated with a silicone-grafted acrylic polymer, dispersed in cyclodimethylsiloxanes "Escalol Z100" from ISP (aluminium oxide-aftertreated ZnO dispersed in an ethylhexyl methoxycinnamate/PVP-hexadecene/methicone copolymer mixture)

"Fuji ZNO-SMS-10" from Fuji Pigment (ZnO aftertreated with silicon dioxide and polymethylsilesquioxane);

Untreated cerium oxide micropigment, for example with the name "Colloidal Cerium Oxide" from Rhone Poulenc Untreated and/or aftertreated iron oxides with the name Nanogar from Arnaud.

For example, it is also possible to employ mixtures of various metal oxides, such as, for example, titanium dioxide and cerium oxide, with and without aftertreatment, such as, for example, the product Sunveil A from Ikeda. In addition, it is also possible to use mixtures of aluminium oxide, silicon dioxide and silicone-aftertreated titanium dioxide. zinc oxide mixtures, such as, for example, the product UV-Titan M261 from Sachtleben, in combination with the UV protection agent according to the invention.

These inorganic UV filters are generally incorporated into the compositions in an amount of 0.1 percent by weight to 25 percent by weight, preferably 2% by weight-10% by weight.

By combination of one or more of the said compounds having a UV filter action, the protective action against harmful effects of the UV radiation can be optimised.

All said UV filters can also be employed in encapsulated form. In particular, it is advantageous to employ organic UV filters in encapsulated form.

The capsules are preferably present in compositions to be employed in accordance with the invention in amounts which ensure that the encapsulated UV filters are present in the composition in the percent by weight ratios indicated above.

Preferred compositions may also comprise at least one further cosmetic active compound, for example selected from antioxidants, anti-ageing active compounds, anti-cellulite active compounds, self-tanning substances, skin-lightening active compounds or vitamins.

Dyes according to the invention can furthermore be combined with all active compounds and assistants as listed systematically in WO2009/098139. In particular, these substances belong to the use categories mentioned therein "moisturisers and humectants", "desquamating agents", "agents for improving the barrier function", "depigmenting agents", "antioxidants", "dermorelaxing or dermo-decontracting agents", "anti-glycation agents", "agents for stimulating the synthesis of dermal and/or epidermal macromolecules and/or for preventing their degradation", "agents for stimulating fibroblast or keratinocyte proliferation and/or keratinocyte differentiation", "agents for promoting the maturation of the horny envelope", "NO-synthase inhibitors", "peripheral benzodiazepine receptor (PBR) antagonists", "agents for increasing the activity of the sebaceous glands", "agents for stimulating the energy metabolism of cells", "tensioning agents", "fat-restructuring agents", "slimming agents", "agents for promoting the cutaneous microcirculation", "calmatives or anti-irritants", "sebo-regulating or anti-seborrhoic agents", "astringents", "cicatrising agents", "anti-inflammatory agents", "antiacne agents".

The protective action of compositions against oxidative stress or against the effect of free radicals can be improved if the compositions comprise one or more antioxidants, the person skilled in the art being presented with absolutely no difficulties in selecting antioxidants which act suitably quickly or with a time delay.

There are many proven substances known from the specialist literature which can be used as antioxidants, for example amino acids (for example glycine, histidine, tyrosine, tryptophan) and derivatives thereof, imidazoles, (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, hexa- and heptathionine sulfoximine) in very low tolerated doses (for example pmol to μmol/kg), and also (metal) chelating agents, (for example α-hydroxyfatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate) and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (for example ZnO, ZnSO$_4$), selenium and derivatives thereof (for example selenomethionine), stilbenes and derivatives thereof (for example stilbene oxide, trans-stilbene oxide).

Suitable antioxidants are also compounds of the formulae A or B

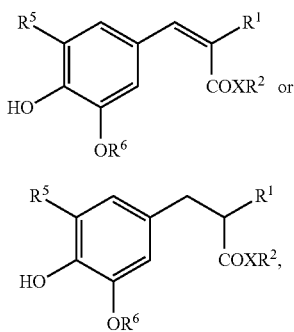

in which
R$^1$ can be selected from the group —C(O)CH$_3$, —CO$_2$R$^3$, —C(O)NH$_2$ and —C(O)N(R$^4$)$_2$,
X denotes O or NH,
R$^2$ denotes linear or branched alkyl having 1 to 30 C atoms,
R$^3$ denotes linear or branched alkyl having 1 to 20 C atoms,
R$^4$ in each case, independently of one another, denotes H or linear or branched alkyl having 1 to 8 C atoms,
R$^5$ denotes H or linear or branched alkyl having 1 to 8 C atoms or linear or branched alkoxy having 1 to 8 C atoms and
R$^6$ denotes linear or branched alkyl having 1 to 8 C atoms, preferably derivatives of 2-(4-hydroxy-3,5-dimethoxybenzylidene)malonic acid and/or 2-(4-hydroxy-3,5-dimethoxybenzyl)malonic acid, particularly preferably bis (2-ethylhexyl) 2-(4-hydroxy-3,5-dimethoxybenzylidene) malonate (for example Oxynex® ST Liquid) and/or bis(2-ethylhexyl) 2-(4-hydroxy-3,5-dimethoxybenzyl)malonate (for example RonaCare® AP).

Furthermore, the combination with bisisopropyl 2-(4-hydroxy-3-methoxybenzylidene)malonate or bisisopropyl 2-(4-hydroxy-3-methoxybenzyl)malonate (hydrogenated diisopropyl vanilidene malonate) is preferred. An analogous situation applies to corresponding bisethyl esters.

Mixtures of antioxidants are likewise suitable for use in the cosmetic compositions according to the invention. Known and commercial mixtures are, for example, mixtures comprising, as active ingredients, lecithin, L-(+)-ascorbyl palmitate and citric acid, natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)ascorbyl palmitate, citric acid and lecithin (for example Oxynex® LM) or butylhydroxytoluene (BHT), L-(+)-ascorbyl palmitate and citric acid (for example Oxynex® 2004). Antioxidants of this type are usually employed in such compositions with the compounds according to the invention in percent by weight ratios in the range from 1000:1 to 1:1000, preferably in percent by weight ratios of 100:1 to 1:100.

Of the phenols which can be used in accordance with the invention, the polyphenols, some of which are naturally occurring, are of particular interest for applications in the pharmaceutical, cosmetic or nutrition sector. For example, the flavonoids or bioflavonoids, which are principally known as plant dyes, frequently have an antioxidant potential.

Quercetin (cyanidanol, cyanidenolon 1522, meletin, sophoretin, ericin, 3,3',4',5,7-pentahydroxyflavone) is frequently mentioned as a particularly effective antioxidant.

Suitable anti-ageing active compounds, in particular for skin-care compositions, are preferably so-called compatible solutes. These are substances which are involved in the osmoregulation of plants or microorganisms and can be isolated from these organisms. The generic term compatible solutes here also encompasses the osmolytes described in German patent application DE-A-10133202. Suitable osmolytes are, for example, the polyols, methylamine compounds and amino acids and respective precursors thereof. Osmolytes in the sense of German patent application DE-A-10133202 are taken to mean, in particular, substances from the group of the polyols, such as, for example, myo-inositol, mannitol or sorbitol, and/or one or more of the osmolytically active substances mentioned below: taurine, choline, betaine, phosphorylcholine, glycerophosphorylcholines, glutamine, glycine, α-alanine, glutamate, aspartate, proline, and taurine. Precursors of these substances are, for example, glucose, glucose polymers, phosphatidylcholine, phosphatidylinositol, inorganic phosphates, proteins, peptides and polyamino acids. Precursors are, for example, compounds which are converted into osmolytes by metabolic steps.

Compatible solutes which are preferably employed in accordance with the invention are substances selected from the group consisting of pyrimidinecarboxylic acids (such as ectoin and hydroxyectoin), proline, betaine, glutamine, cyclic diphosphoglycerate, N.-acetylornithine, trimethylamine N-oxide di-myo-inositol phosphate (DIP), cyclic 2,3-diphosphoglycerate (cDPG), 1,1-diglycerol phosphate (DGP), β-mannosyl glycerate (firoin), β-mannosyl glyceramide (firoin-A) or/and dimannosyl diinositol phosphate (DMIP) or an optical isomer, derivative, for example an acid, a salt or ester, of these compounds, or combinations thereof.

Of the pyrimidinecarboxylic acids, particular mention should be made here of ectoin ((S)-1,4,5,6-tetrahydro-2-methyl-4-pyrimidinecarboxylic acid) and hydroxyectoin ((S,S)-1,4,5,6-tetrahydro-5-hydroxy-2-methyl-4-pyrimidinecarboxylic acid) and derivatives thereof.

Anti-ageing active compounds which can be used are additionally products from Merck, such as, for example, 5,7-dihydroxy-2-methylchromone, marketed under the trade name RonaCare®Luremine, or the commercial products Ronacare®Isoquercetin, Ronacare®Tilirosid or Ronacare® Cyclopeptide 5.

Furthermore, the compositions according to the invention may comprise at least one self-tanning agent as further ingredient.

Advantageous self-tanning agents which can be employed are, inter alia: 1,3-dihydroxyacetone, glycerolaldehyde, hydroxymethylglyoxal, γ-dialdehyde, erythrulose, 6-aldo-D-fructose, ninhydrin, 5-hydroxy-1,4-naphtoquinone (juglone) or 2-hydroxy-1,4-naphtoquinone (lawsone). Very particular preference is given to 1,3-dihydroxyacetone, erythrulose or a combination thereof.

The compositions may also comprise one or more further skin-lightening active compounds or synonymously depigmentation active compounds. Skin-lightening active compounds can in principle be all active compounds known to the person skilled in the art. Examples of compounds having skin-lightening activity are hydroquinone, kojic acid, arbutin, aloesin or rucinol.

The compositions to be employed may comprise vitamins as further ingredients. Preference is given to vitamins and vitamin derivatives selected from vitamin A, vitamin A propionate, vitamin A palmitate, vitamin A acetate, retinol, vitamin B, thiamine chloride hydrochloride (vitamin $B_1$), riboflavin (vitamin $B_2$), nicotinamide, vitamin C (ascorbic acid), vitamin D, ergocalciferol (vitamin $D_2$), vitamin E, DL-α-tocopherol, tocopherol E acetate, tocopherol hydrogensuccinate, vitamin $K_1$, esculin (vitamin P active compound), thiamine (vitamin $B_1$), nicotinic acid (niacin), pyridoxine, pyridoxal, pyridoxamine, (vitamin $B_6$), panthothenic acid, biotin, folic acid and cobalamine (vitamin $B_{12}$), particularly preferably vitamin A palmitate, vitamin C and derivatives thereof, DL-α-tocopherol, tocopherol E acetate, nicotinic acid, pantothenic acid and biotin. In the case of cosmetic application, vitamins are usually added with the flavonoid-containing premixes or compositions in ranges from 0.01 to 5.0% by weight, based on the total weight. Nutritionphysiological applications are oriented towards the respective recommended vitamin requirement.

The retinoids described are at the same time also effective anti-cellulite active compounds. A likewise known anti-cellulite active compound is caffeine.

The said constituents of the composition can be incorporated in the usual manner, with the aid of techniques which are well known to the person skilled in the art.

Suitable compositions are those for external application, for example can be sprayed onto the skin as cream or milk (O/W, W/O, O/W/O, W/O/W), as lotion or emulsion, in the form of oily-alcoholic, oily-aqueous or aqueousalcoholic gels or solutions. They can be in the form of solid sticks or formulated as an aerosol. Administration forms such as capsules, dragees, powders, tablet solutions or solutions are suitable for internal use.

Examples which may be mentioned of application forms of the compositions to be employed are: solutions, suspensions, emulsions, PIT emulsions, pastes, ointments, gels, creams, lotions, powders, soaps, surfactant-containing cleansing preparations, oils, aerosols and sprays.

Preferred assistants originate from the group of preservatives, stabilisers, solubilisers, colorants, odour improvers.

Ointments, pastes, creams and gels may comprise the customary vehicles which are suitable for topical application, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary vehicles, for example lactose, talc, silica, aluminium hydroxide, calcium silicate and polyamide powder, or mixtures of these substances. Sprays may additionally comprise the customary readily volatile, liquefied propellants, for example chlorofluorocarbons, propane/butane or dimethyl ether. Compressed air can also advantageously be used.

Solutions and emulsions may comprise the customary vehicles, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, glycerol fatty acid esters, polyethylene glycols and fatty acid esters of sorbitan, or mixtures of these substances.

A preferred solubiliser in general is 2-isopropyl-5-methyl-cyclohexanecarbonyl-D-alanine methyl ester.

Suspensions may comprise the customary vehicles, such as liquid diluents, for example water, ethanol or propylene glycol, suspension media, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary vehicles, such as alkali metal salts of fatty acids, salts of fatty acid monoesters, fatty acid protein hydrolysates, isothionates, lanolin, fatty alcohol, vegetable oils, plant extracts, glycerol, sugars, or mixtures of these substances.

Surfactant-containing cleansing products may comprise the customary vehicles, such as salts of fatty alcohol sulfates, fatty alcohol ether sulfates, sulfosuccinic acid monoesters, fatty acid protein hydrolysates, isothionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary vehicles, such as synthetic oils, such as fatty acid esters, fatty alcohols, silicone oils, natural oils, such as vegetable oils and oily plant extracts, paraffin oils, lanolin oils, or mixtures of these substances.

Further typical cosmetic application forms are also lipsticks, lip-care sticks, powder make-up, emulsion make-up and wax make-up, and sunscreen, pre-sun and after-sun preparations.

The preferred composition forms also include, in particular, emulsions.

Emulsions are advantageous and comprise, for example, the said fats, oils, waxes and other fatty substances, as well as water and an emulsifier, as usually used for a composition of this type.

The lipid phase may advantageously be selected from the following group of substances:

mineral oils, mineral waxes
oils, such as triglycerides of capric or caprylic acid, furthermore natural oils, such as, for example, castor oil;
fats, waxes and other natural and synthetic fatty substances, preferably esters of fatty acids with alcohols having a low carbon number, for example with isopropanol, propylene glycol or glycerol, or esters of fatty alcohols with alkanoic acids having a low carbon number or with fatty acids;
silicone oils, such as dimethylpolysiloxanes, diethylpolysiloxanes, diphenylpolysiloxanes, and mixed forms thereof.

For the purposes of the present invention, the oil phase of the emulsions, oleogels or hydrodispersions or lipodispersions is advantageously selected from the group of esters of saturated and/or unsaturated, branched and/or unbranched alkanecarboxylic acids having a chain length of 3 to 30 C atoms and saturated and/or unsaturated, branched and/or unbranched alcohols having a chain length of 3 to 30 C atoms, from the group of esters of aromatic carboxylic acid and saturated and/or unsaturated, branched and/or unbranched alcohols having a chain length of 3 to 30 C atoms. Ester oils of this type can then advantageously be selected from the group isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of esters of this type, for example jojoba oil.

The mixture according to the invention may preferably comprise assistants, such as, for example, cosmetic oils (for example Caprylic/Capric Triglycerides, C12-15 Alkyl Benzoate, isopropyl myristate, Arylalkyl Benzoate, such as, for example, phenethyl benzoate (X-Tend 226) or oil components of the Cosmacol brand, such as Dimyristyl Tartrate, Tri C14-C15 Alkyl Citrate, C12-C13 Alkyl Lactate, Tridecyl Salicylate, C12-C13 Alkyl Octanoate, C12-C13 Alkyl Malate, C12-C13 Alkyl Citrate, C12-C13 Alkyl Tartrate), or polarprotic assistants (for example propylene glycol, glycerine, isopropanol, ethanol) or so-called solubilisers (for example butylphthalimides, isopropylphthalimides, dimethylisosorbides).

The oil phase may furthermore advantageously be selected from the group of branched and unbranched hydrocarbons and hydrocarbon waxes, silicone oils, dialkyl ethers, the group of saturated or unsaturated, branched or unbranched alcohols, and fatty acid triglycerides, specifically the triglycerol esters of saturated and/or unsaturated, branched and/or unbranched alkanecarboxylic acids having a chain length of 8 to 24, in particular 12-18 C atoms. The fatty acid triglycerides may, for example, advantageously be selected from the group of synthetic, semi-synthetic and natural oils, for example olive oil, sunflower oil, soya oil, peanut oil, rapeseed oil, almond oil, palm oil, coconut oil, palm kernel oil and the like.

Any desired mixtures of oil and wax components of this type may also advantageously be employed for the purposes of the present invention. It may also be advantageous to employ waxes, for example cetyl palmitate, as sole lipid component of the oil phase.

The aqueous phase of the compositions to be employed optionally advantageously comprises alcohols, diols or polyols having a low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols having a low carbon number, for example ethanol, isopropanol, 1,2-propanediol, glycerol, and, in particular, one or more thickeners, which may advantageously be selected from the group silicon dioxide, aluminium silicates, polysaccharides and derivatives thereof, for example hyaluronic acid, xanthan gum, hydroxypropylmethylcellulose, particularly advantageously from the group of the polyacrylates, preferably a polyacrylate from the group of the so-called Carbopols, for example Carbopol grades 980, 981, 1382, 2984, 5984, in each case individually or in combination.

In particular, mixtures of the above-mentioned solvents are used. In the case of alcoholic solvents, water may be a further constituent.

Emulsions are advantageous and comprise, for example, the said fats, oils, waxes and other fatty substances, as well as water and an emulsifier, as usually used for a formulation of this type.

In a preferred embodiment, the compositions to be employed comprise hydrophilic surfactants. The hydrophilic surfactants are preferably selected from the group of the alkylglucosides, acyl lactylates, betaines and coconut amphoacetates.

It is likewise advantageous to employ natural or synthetic raw materials and assistants or mixtures which are distinguished by an effective content of the active compounds used in accordance with the invention, for example Plantaren® 1200 (Henkel KGaA), Oramix® NS10 (Seppic).

The cosmetic and dermatological compositions may exist in various forms. Thus, they may be, for example, a solution, a water-free composition, an emulsion or microemulsion of the water-in-oil (W/O) type or of the oil-inwater (O/W) type, a multiple emulsion, for example of the water-in-oil-inwater (W/O/W) type, a gel, a solid stick, an ointment or an aerosol. It is also advantageous to administer ectoins in encapsulated form, for example in collagen matrices and other conventional encapsulation materials, for example as cellulose encapsulations, in gelatine, wax matrices or liposomally encapsulated. In particular, wax matrices, as described in DE-A-43 08 282, have proven favourable. Preference is given to emulsions. O/W emulsions are particularly preferred. Emulsions, W/O emulsions and O/W emulsions are obtainable in a conventional manner.

Emulsifiers that can be used are, for example, the known W/O and O/W emulsifiers. It is advantageous to use further conventional co-emulsifiers in the preferred O/W emulsions.

The co-emulsifiers selected are advantageously, for example, O/W emulsifiers, principally from the group of substances having HLB values of 11-16, very particularly advantageously having HLB values of 14.5-15.5, so long as the O/W emulsifiers have saturated radicals R and R'. If the O/W emulsifiers have unsaturated radicals R and/or R', or if isoalkyl derivatives are present, the preferred HLB value of such emulsifiers may also be lower or higher.

It is advantageous to select the fatty alcohol ethoxylates from the group of the ethoxylated stearyl alchols, cetyl alcohols, cetylstearyl alcohols (cetearyl alcohols).

It is furthermore advantageous to select the fatty acid ethoxylates from the following group:
polyethylene glycol (20) stearate, polyethylene glycol (21) stearate, polyethylene glycol (22) stearate, polyethylene glycol (23) stearate, polyethylene glycol (24) stearate, polyethylene glycol (25) stearate, polyethylene glycol (12) isostearate, polyethylene glycol (13) isostearate, polyethylene glycol (14) isostearate, polyethylene glycol (15) isostearate, polyethylene glycol (16) isostearate, polyethylene glycol (17) isostearate, polyethylene glycol (18) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24) isostearate, polyethylene glycol (25) isostearate, polyethylene glycol (12) oleate, polyethylene glycol (13) oleate, polyethylene glycol (14) oleate, polyethylene glycol (15) oleate, polyethylene glycol (16) oleate, polyethylene glycol (17) oleate, polyethylene glycol (18) oleate, polyethylene glycol (19) oleate, polyethylene glycol (20) oleate.

An ethoxylated alkyl ether carboxylic acid or salt thereof which can advantageously be used is sodium laureth-11 carboxylate. An alkyl ether sulfate which can advantageously be used is sodium laurethyl-4 sulfate. An ethoxylated cholesterol derivative which can advantageously be used is polyethylene glycol (30) cholesteryl ether. Polyethylene glycol (25) soyasterol has also proven successful. Ethoxylated triglycerides which can advantageously be used are the polyethylene glycol (60) evening primrose glycerides.

It is furthermore advantageous to select the polyethylene glycol glycerol fatty acid esters from the group polyethylene glycol (20) glyceryl laurate, polyethylene glycol (21) glyceryl laurate, polyethylene glycol (22) glyceryl laurate, polyethylene glycol (23) glyceryl laurate, polyethylene glycol (6) glyceryl caprate/cprinate, polyethylene glycol (20) glyceryl oleate, polyethylene glycol (20) glyceryl isostearate, polyethylene glycol (18) glyceryl oleate (cocoate).

It is likewise favourable to select the sorbitan esters from the group polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

The following can be employed as optional W/O emulsifiers, but ones which may nevertheless be advantageous in accordance with the invention: fatty alcohols having 8 to 30 carbon atoms, monoglycerol esters of saturated and/or unsaturated, branched and/or unbranched alkanecarboxylic acids having a chain length of 8 to 24, in particular 12-18 C atoms, diglycerol esters of saturated and/or unsaturated, branched and/or unbranched alkanecarboxylic acids having a chain length of 8 to 24, in particular 12-18 C atoms, monoglycerol ethers of saturated and/or unsaturated, branched and/or unbranched alcohols having a chain length of 8 to 24, in particular 12-18 C atoms, diglycerol ethers of saturated and/or unsaturated, branched and/or unbranched alcohols having a chain length of 8 to 24, in particular 12-18 C atoms, propylene glycol esters of saturated and/or unsaturated, branched and/or unbranched alkanecarboxylic acids having a chain length of 8 to 24, in particular 12-18 C atoms, and sorbitan esters of saturated and/or unsaturated, branched and/or unbranched alkanecarboxylic acids having a chain length of 8 to 24, in particular 12-18 C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate, glyceryl monocaprylate or PEG-30 dipolyhydroxystearate.

The composition may comprise cosmetic adjuvants which are usually used in this type of composition, such as, for example, thickeners, softeners, moisturisers, surface-active agents, emulsifiers, preservatives, antifoams, perfumes, waxes, lanolin, propellants, dyes and/or pigments, and other ingredients usually used in cosmetics.

The dispersant or solubiliser used can be an oil, wax or other fatty substance, a lower monoalcohol or a lower polyol or mixtures thereof. Particularly preferred monoalcohols or polyols include ethanol, i-propanol, propylene glycol, glycerol and sorbitol.

A preferred embodiment of the invention is an emulsion which is in the form of a protective cream or milk and comprises, for example, fatty alcohols, fatty acids, fatty acid esters, in particular triglycerides of fatty acids, lanolin, natural and synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

The composition may also be in the form of an alcoholic gel which comprises one or more lower alcohols or polyols, such as ethanol, propylene glycol or glycerol, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other fatty substances.

If a composition is formulated as an aerosol, use is generally made of the customary propellants, such as alkanes, fluoroalkanes and chlorofluoroalkanes, preferably alkanes.

Even without further comments, it is assumed that a person skilled in the art will be able to utilise the above description in the broadest scope. The preferred embodiments and examples should therefore merely be regarded as descriptive disclosure which is absolutely not limiting in any way. The complete disclosure content of all applications and publications mentioned above and below is incorporated into this application by way of reference. The percent by weight ratios of the individual ingredients in the compositions of the examples expressly belong to the disclosure content of the description and can therefore be utilised as features.

Further important features and advantages of the invention arise from the sub-claims and from the examples.

It goes without saying that the features mentioned above and still to be explained below can be used not only in the respective combination indicated, but also in other combinations or in isolation without leaving the context of the present invention.

Preferred embodiments of the invention are described in the examples and are explained in greater detail in the following description without restricting the scope of the present invention.

Compositions:

General Notes:

Described ascorbates of the formula I of azo compounds of the formula V can be incorporated both into the oil phase of compositions, such as, for example, emulsions, and also into the water phase thereof. Combined incorporation into the oil and water phase is preferably also possible. For incorporation into the oil or water phase, the use of solubility promoters is advantageous. For example, the addition of alcohol components (e.g. ethanol, isopropanol) is advantageous here. The pH of the formulation should preferably be between pH=3 and pH=7 in order to achieve satisfactory stability of the ascorbate through an acidic environment in the formulation. It is particularly preferred, for example, to buffer the pH of the water phase to pH=5 using citrate buffer, since this corresponds to the natural pH of the skin. In general, the ascorbates described can be incorporated into at least one lipophilic or hydrophilic phase of a composition in such a way that either a clear solution is present or the substances are in dispersed form.

The following substance codes are used in the following formulation examples:

Dye A: (R)-2-((R)-3,4-Dihydroxy-5-oxo-2,5-dihydrofuran-2-yl)-2-hydroxyethyl 4-phenylazobenzoate

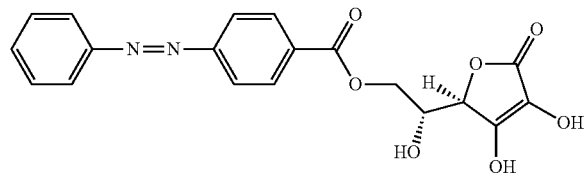 [SMILES: O=C1O[C@H]([C@H](O)COC(=O)c2ccc(N=Nc3ccccc3)cc2)C(O)=C1O]

Dye B: (R)-2-((R)-3,4-Dihydroxy-5-oxo-2,5-dihydrofuran-2-yl)-2-hydroxyethyl 4-(4-dimethylaminophenylazo)benzoate

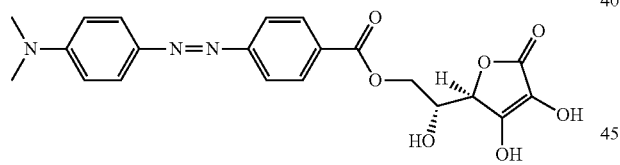

Dye C: 2-(R)-((R)-(3,4-Dihydroxy-5-oxo-2,5-dihydrofuran-2-yl)-2-hydroxyethyl 4-(4-dimethylaminophenylazo)phenylsulfonate

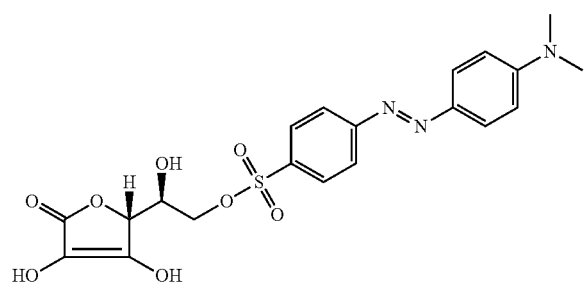 [SMILES: CN(C)c1ccc(/N=N/c2ccc(S(=O)(=O)OC[C@H](O)[C@H]3OC(=O)C(O)=C3O)cc2)cc1]

Dye D: (R)-2-((R)-3,4-Dihydroxy-5-oxo-2,5-dihydrofuran-2-yl)-2-hydroxyethyl 2-(5-hydroxy-3-methyl-1-phenyl-1H-pyrazol-4-ylazo)benzoate

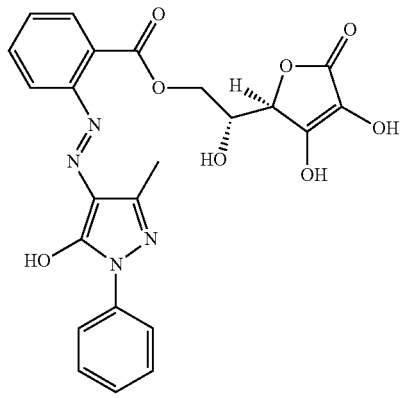 [SMILES: Cc1nn(-c2ccccc2)c(O)c1/N=N/c1ccccc1C(=O)OC[C@@H](O)[C@H]1OC(=O)C(O)=C1O]

SYNTHESIS EXAMPLES

Synthesis Example 1

Synthesis of Dye A 2.5 g of para-phenylazobenzoic acid (11.05 mmol, 1 eq.) are dissolved in a mixture of 12 ml of NMP (N-methyl-2-pyrrolidone) and 26 ml of acetonitrile. 0.96 ml of thionyl chloride (13.26 mmol, 1.2 eq.) are added at room temperature, and the mixture is stirred at room temperature for 3 h. 3.9 g of L-ascorbic acid (22 mmol, 2 eq.) are subsequently added, and the mixture is stirred at room temperature for 16 hours. 70 ml of 2N HCl are added to the reaction solution. The precipitated solid is filtered off with suction and suspended with 50 ml of dichloromethane. Filtration and drying thus give the product as orange-brown solid with a yield of 66% (2.7 g).

$^{1}$H-NMR (400 MHz, DMSO) δ=4.19 (t, CH, J=5.5 Hz), 4.32 (dd, CH$_2$, J=5.5 Hz, J=10.5 Hz), 4.41 (dd, CH$_2$, J=5.5 Hz, J=10.5 Hz), 4.79 (d, CH, J=1.2 Hz), 5.52 (br, OH), 7.47 (m, 2×Ar—H), 7.82 (m, 2×Ar—H), 7.87 (d, 2×Ar—H, J=8.3 Hz), 8.13 (d, 2×Ar—H, J=8.3 Hz), 11.15 (br, OH) ppm.

$^{13}$C-NMR (75 MHz, DMSO) δ=65.68, 65.80, 75.14, 118.27, 122.58, 122.83, 129.55, 130.59, 131.52, 132.26, 151.89, 152.01, 154.50, 164.93, 170.27 ppm.

Synthesis Example 2

Synthesis of Dye B 2.5 g of para-4-(4-dimethylaminophenylazo)benzoic acid 9.28 mmol, 1 eq.) are suspended in a mixture of 15 ml of NMP and 30 ml of acetonitrile. 0.808 ml of thionyl chloride (11.14 mmol, 1.2 eq.) are added at room temperature, and the mixture is stirred at room temperature for 3 h. 3.27 g of L-ascorbic acid (19 mmol, 2 eq.) are subsequently added, and the mixture is stirred at room temperature for 24 hours. 70 ml of 2N HCl are added to the reaction solution. The precipitated solid is filtered off with suction and suspended with 80 ml of dichloromethane. Filtration and drying thus give the product as red-brown solid with a yield of 76% (3 g).

Synthesis Example 3

Synthesis of Dye C 5,6-Isopropylidene L-ascorbate (10 g; 46.3 mmol, 1 eq.) is dissolved in 30 ml of THF and 35 ml of DMSO, 19.2 g of potassium carbonate are added, and 13 ml of benzyl bromide (110 mmol, 2.4 eq.) are added dropwise. After 3 hrs at 50° C., the evolution of gas is complete. The solid is filtered off and extracted 3 times with 100 ml of ethyl acetate each time. The combined organic phases are dried over sodium sulfate, and the solvent is removed in vacuo, giving 2,3-dibenzyl-5,6-isopropylidene ascorbate virtually quantitatively without further purification.

The di-benzyl-protected 5,6-isopropylidene L-ascorbate is dissolved in 65 ml of THF, and 30 ml of 2 N HCl are slowly added at room temperature. After 48 hrs, 150 ml of MTBE (methyl tert-butyl ether) and solid sodium chloride are added to saturation, and the mixture is extracted. The organic phase is dried over sodium sulfate, and the solvent is removed in vacuo, giving 2,3-dibenzyl L-ascorbate virtually quantitatively without further purification.

The di-benzyl-protected L-ascorbic acid (2.14 g; 6 mmol, 1 eq.) is dissolved in 11 ml of dichloromethane. Triethylamine (0.91 g; 9 mmol, 1.5 eq.) and dabsyl chloride (2.3 g; 7.2 mmol, 1.2 eq.) are then added at 0° C. The mixture is warmed to room temperature (RT), and, after 22 hrs, the solvent is removed in vacuo. The residue is extracted with 50 ml of ethyl acetate and 50 ml of sat. NaCl soln. The organic phase is dried over sodium sulfate, and the solvent is removed in vacuo. The crude product formed is dissolved in 50 ml of ethyl acetate and reduced under a hydrogen pressure of 5 bar with 2% by weight of Pd/C catalyst. After filtration of the catalyst, the product is purified by filtration through 300 g of silica gel and 1500 ml of ethyl acetate, giving the dye C as orange solid.

Synthesis Example 4

Synthesis of Dye D 10 g of 2-(5-hydroxy-3-methyl-1-phenyl-1H-pyrazol-4-ylazo)benzoic acid (31.03 mmol) are dissolved in 120 ml of dioxane, 6.7 g of DCC (dicyclohexylcarbodiimide) (32.58 mmol, 1.05 eq.) and subsequently, in portions, a total of 10.93 g of L-ascorbic acid (62 mmol, 2 eq.) are added. After a reaction time of 13 h at room temperature, 80% of the solvent is distilled off. 150 ml of water are added, and the solid formed is filtered off and washed with water. The product is subsequently purified by suspension three times in 100 ml of isopropanol each time, giving 8.3 g of the dye D (56%) as yellow solid.

Example 1

Textile Colouring

Dye B and dye A are dissolved/dispersed in water to the extent of 5% each. The pH of the water is alkaline. The aqueous solution/dispersion is firstly boiled and subsequently cooled slowly to below 40° C., before the wool is added (about 1 kg of wool per 25-30 litres of water). After 24 h, the wool is removed and rinsed well with tap water.

Example 2

Hair Dye Comprising Various Components

Component A:
Tocopherol, Linalool, Geraniol, Disodium EDTA, perfume, ascorbic acid, alcohol denat., Sodium sulfite, Sodium hydroxide, Sodium cocoyl isethionate, Bis-ethylhexyl Hydroxydimethoxy Benzylmalonate, Sodium lauryl sulfate, Ammonia, Lanolin alcohol, Glycol distearate, Sodium laureth sulfate, Glyceryl stearate, Ceteary alcohol, Aqua.
Component B:
Aqua, hydrogen peroxide, cetearyl alcohol, PPG-38-buteth-37, petrolatum, laureth-2, sodium cetearyl sulfate, salicylic acid, disodium phosphate, phosphoric acid, etidronic acid.
Component C:
Ethanolic solution of dye A and/or B (2% by weight each) additionally containing Bis-ethylhexyl Hydroxydimethoxy Benzylmalonate (1% by weight).
Component D:
Ethanolic solution of Bis-ethylhexyl Hydroxydimethoxy Benzylmalonate (1% by weight).
Use:
For hair colouring, the following procedure is preferably followed in the following sequence: firstly, the hair is pretreated with component C, components B and C are subsequently mixed and applied to the hair. When the colouring is complete, component D is applied.

Example 3

Hair Dye Comprising Various Components

Component A:
Tocopherol, Linalool, Geraniol, Disodium EDTA, perfume, Toluene-2,5-diamine sulfate, ascorbic acid, alcohol denat., Sodium sulfite, Sodium hydroxide, Sodium cocoyl isethionate, Bis-ethylhexyl Hydroxydimethoxy Benzylmalonate, 2-Methylresorcinol, 6-Amino-m-cresol, 4-Amino-2-hydroxytoluene, 4-Amino-m-cresol, Sodium lauryl sulfate, Ammonia, Lanolin alcohol, Glycol distearate, Sodium laureth sulfate, Glyceryl stearate, Ceteary alcohol, Aqua.
Component B:
Aqua, hydrogen peroxide, cetearyl alcohol, PPG-38-buteth-37, petrolatum, laureth-2, sodium cetearyl sulfate, salicylic acid, disodium phosphate, phosphoric acid, etidronic acid.
Component C:
Ethanolic solution of dye A and/or B (2% by weight each) additionally containing Bis-ethylhexyl Hydroxydimethoxy Benzylmalonate (1% by weight).
Component D:
Ethanolic solution of Bis-ethylhexyl Hydroxydimethoxy Benzylmalonate (1% by weight).
Use:
For hair colouring, the following procedure is preferably followed in the following sequence: firstly, the hair is pretreated with component C, components B and C are subsequently mixed and applied to the hair. When the colouring is complete, component D is applied.

All illustrative formulations of the compositions can optionally also be prepared without UV filters.

Example 4

W/O Emulsion

|  | a | b | c | d | e |
|---|---|---|---|---|---|
| Cetyl PEG/PPG-10/1 dimethicone (Abil EM 90) | 3.00 | 3.00 | 3.00 | 3.00 | 3.00 |

-continued

|  | a | b | c | d | e |
|---|---|---|---|---|---|
| Polyglyceryl-4 isostearate (Isolan GI 34) | 1.50 | 1.50 | 1.50 | 1.50 | 1.50 |
| Butylphthalimide isopropylphthalimide (Pelemol ® BIP) | 5.00 | 5.00 | 5.00 | 5.00 | 5.00 |
| Dimethyl isosorbide (Arlasolve DMI) | 5.00 | 5.00 | 5.00 | 5.00 | 5.00 |
| Dye A | 2.00 |  |  |  | 1.00 |
| Dye B |  | 2.00 |  |  | 1.00 |
| Dye C |  |  | 2.00 |  | 1.00 |
| Dye D |  |  |  | 2.00 | 1.00 |
| Uvinul ® A Plus (DHHB) |  | 1.00 | 1.00 | 1.00 |  |
| Ascorbic acid |  |  | 0.37 | 1.00 | 3.00 |
| Mineral Oil | 8.00 | 8.00 | 8.00 | 8.00 | 8.00 |
| Ethylhexyl stearate (Tegosoft ® OS) | 5.00 | 5.00 | 5.00 | 5.00 | 5.00 |
| Cyclomethicone (and) Aluminium/Magnesium Hydroxide Stearate (Gilugel SIL 5) | 5.00 | 5.00 | 5.00 | 5.00 | 5.00 |
| Preservative | 1.00 | 1.00 | 1.00 | 1.00 | 1.00 |
| Water | To 100 | To 100 | To 100 | To 100 | To 100 |
| NaCl | 0.50 | 0.50 | 0.50 | 0.50 | 0.50 |
| EDTA | 0.10 | 0.10 | 0.10 | 0.10 | 0.10 |
| Citric acid q.S. | | | | | |

Preparation: Pelemol BIP, Arlasolv DMI and emulsifiers are initially introduced. Dyes A-D and Uvinul® A Plus are dissolved therein. The remaining constituents of the oil phase are added and mixed homogeneously. The water phase, adjusted to pH=4-5 using citric acid, is emulsified in with stirring. The mixture is subsequently homogenised. The emulsions can be prepared under gentle conditions at room temperature. By increasing the content of ascorbic acid, dye ascorbates present can be stabilised. The preparation is ideally with inertisation (exclusion of oxygen prepared).

Example 5

Water-resistant Sunscreen Spray with Application Control

| A | | | |
|---|---|---|---|
| Dye A | 1.00 | 1.00 | 2.00 |
| Diethylhexyl Syringylidenemalonate, Caprylic/Capric Triglyceride (Oxynex ® ST Liquid) |  | 0.50 |  |
| RonaCare ® AP |  | 2.00 |  |
| Ascorbyl Palmitate |  |  | 1.00 |
| Cyprylic/capric Triglyceride (Miglyol 812 N) | 7.00 | 7.00 | 7.00 |
| Butylphthalimide isopropylphthalimide (Pelemol ® BIP) | 9.00 | 9.00 | 9.00 |
| C12-15 alkyl benzoate (Tegosoft ® TN) | 10.00 | 10.00 | 10.00 |
| Phenethyl benzoate (X-Tend 226) | 5.00 | 5.00 | 5.00 |
| RonaCare ® tocopherol acetate | 1.00 | 1.00 | 1.00 |
| B | | | |
| Cyclopentasiloxane (Dow Corning 245) | 43.80 | 41.30 | 41.80 |
| Phenyltrimethicone (Dow Corning 556) | 2.00 | 2.00 | 2.00 |
| Cyclopentasiloxane, dimethiconol Dow Corning 1501 Fluid | 20.00 | 20.00 | 20.00 |
| Perfume oil (q.s.) | 0.20 | 0.20 | 0.20 |

Preparation: the components of phase A are combined at room temperature and stirred until a clear solution or homogeneous dispersion is present. Phase B is subsequently mixed and added to phase B with stirring. Stirring is continued until the homogeneous product is finally present. To addition of antioxidants, such as Oxynex® ST Liquid, RonaCare® AP or ascorbyl palmitate, the stability of the substances according to the invention can be increased.

Example 6

Pump Hair-tinting Spray

| A | | | |
|---|---|---|---|
| Dye A | 1.00 | 1.00 | 4.00 |
| Dye B | 1.00 |  |  |
| Dye C |  | 1.00 |  |
| Dye D |  |  | 1.00 |
| Ethanol 96% extra pure | To 100 | To 100 | To 100 |
| PVP/VA copolymer PVP/VA W 735 | 6.00 | 6.00 | 6.00 |
| B | | | |
| Diethylhexyl Syringylidenemalonate, Caprylic/Capric Triglyceride (Oxynex ® ST Liquid) | 0.06 | 0.25 | 0.50 |
| PEG-75 Lanolin BHT (Solan E-Low Dioxane) | 0.20 | 0.20 | 0.20 |
| Perfume (Frag 280853 Green Activating) | 0.10 | 0.10 | 0.10 |
| C | | | |
| Water, demineralised | 13.00 | 13.00 | 13.00 |
| Titriplex III | 0.10 | 0.10 | 0.10 |
| PEG-12 dimethicone Dow Corning 193 Fluid | 0.50 | 0.50 | 0.50 |
| 0.1% D&C Red No 33 (CI 17200) in water | 0.20 | 0.20 | 0.20 |
| PEG-40 Hydrogenated Castor Oil (Cremophor RH 410) | 1.00 | 1.00 | 1.00 |

Preparation: pre-dissolve phase A until a clear solution is present. Add phase B to phase A with stirring. Pre-mix phase C and add to the remainder, stir until a homogeneous mixture has formed.

Example 7

W/O Emulsions

| Emulsion | A | B | C | D | E | F |
|---|---|---|---|---|---|---|
| Polyglyceryl 2-dipolyhydroxystearate | 3 | 5 | 3 |  |  |  |
| PEG-30 dipolyhydroxystearate |  |  |  | 2 | 3 | 4 | 5 |
| Sodium starch octenylsuccinate | 0.5 | 0.4 |  | 0.3 |  | 1 |
| Glycine | 0.3 | 0.3 | 0.5 | 0.4 |  |  |
| Alcohol |  | 5 | 2 | 5 | 4 |  |

-continued

| Emulsion | A | B | C | D | E | F |
|---|---|---|---|---|---|---|
| Magnesium sulfate | 0.2 | 0.3 | 0.3 | 0.4 | 0.5 | 0.2 |
| $C_{12-15}$ Alkyl benzoate | 5 | 3 | | | 5 | 5 |
| $C_{12-13}$ Alkyl tartrate | | | 2 | | | |
| Butylene glycol dicaprylate/dicaprate | 5 | | | | 3 | 3 |
| Dicaprylyl Ether | | | | 2 | | |
| Mineral oil | | 4 | | 6 | | 8 |
| Octyldodecanol | 2 | | | | | |
| Dicapryl caprate | | | 2 | | 2 | 2 |
| Cyclomethicone | 5 | | 5 | 10 | | |
| Dimethicone | | | | 5 | | |
| Isohexadecane | | 1 | | | | |
| Butylene glycol | 5 | 8 | | | | 3 |
| Propylene glycol | | | 1 | | 5 | 3 |
| Glycerine | 3 | 5 | 7 | 10 | 3 | 3 |
| C18-38 acid triglycerides | 0.5 | | 1 | | 1 | |
| Titanium dioxide | 5 | 6 | 4 | | | 4 |
| Zinc oxide | 5 | | | | | |
| Bis-ethylhexyloxyphenol methoxyphenyltriazine | | 3 | 3 | 2 | | |
| Ethylhexyltriazone | | 4.5 | 3 | | 3 | |
| Dye A | 1.0 | | 1.5 | 1.0 | 3.0 | |

-continued

| Emulsion | A | B | C | D | E | F |
|---|---|---|---|---|---|---|
| Diethylhexylbutamidotriazone | | | 1.5 | 4 | | |
| Butylmethoxydibenzoyl-methane | 2 | 3 | 4 | | 1 | 3 |
| Uvinul ® A Plus | | | | 4 | 2 | |
| Ethylhexyl methoxycinnamate | | | | | 7 | 5 |
| Dye B | | 4.0 | 0.5 | 1.5 | | 0.5 |
| Taurine | 0.1 | | | 0.5 | 0.2 | |
| Vitamin E acetate | 0.2 | 02 | | 0.3 | 0.1 | 0.5 |
| $Na_2H_2EDTA$ | 0.1 | 0.1 | 0.2 | 0.2 | 0.2 | 0.5 |
| C8-C16 alkylpolyglycoside | 1 | | | | | |
| Perfume, preservative | q.s. | q.s | q.s. | q.s. | q.s. | qs. |
| Dyes, etc. | q.s. | q.s. | q.s. | q.s | q.s. | q.s. |
| Sodium hydroxide | q.s. | q.s. | q.s. | q.s | q.s. | q.s. |
| Water | to 100.0 | to 100.0 | to 100.0 | to 100.0 | to 100.0 | to 100.0 |

Example 8

Hair-care Formulation

| | Content in g of component per 100 g of formulation | | | | | |
|---|---|---|---|---|---|---|
| Component | A | B | C | D | E | F |
| Disodium EDTA | 0.100 | 0.100 | 0.100 | 0.100 | 0.100 | 0.100 |
| Oxynex ®ST | 2.000 | 2.000 | 2.000 | 2.000 | 2.000 | 2.000 |
| Dye A | 0.10 | 0.25 | 0.50 | 1.50 | 2.00 | 4.00 |
| Dye C | 0.50 | 1.00 | 1.50 | 2.00 | 2.50 | 3.00 |
| Hexamidine diisethionate | 0.100 | 0 | 0 | 0 | 0 | 0 |
| Tetrahydrocurcumin | 0 | 0.500 | 0 | 0 | 0 | 0 |
| Glycyrrhetinic acid | 0 | 0 | 0.300 | 0 | 0 | 0 |
| Thiotaine ®[1] | 0 | 0 | 0 | 5.000 | 0 | 0 |
| N-undecylenoyl-L-phenylalanine | 0 | 0 | 0 | 0 | 1.000 | 0 |
| N-acetyl glucosamine | 0 | 0 | 0 | 0 | 0 | 2.000 |
| Niacinamide | 5.000 | 5.000 | 5.000 | 5.000 | 5.000 | 5.000 |
| Citric acid | 0.015 | 0 | 0 | 0 | 0 | 0 |
| Isohexadecane | 3.000 | 3.000 | 3.000 | 3.000 | 3.000 | 3.000 |
| Isopropyl isostearate | 1.330 | 1.330 | 1.330 | 1.330 | 1.330 | 1.330 |
| Isopropyl N-laurosylsarcosinate | 0 | 0 | 5.000 | 0 | 0 | 0 |
| Sucrose polycottonseedate | 0.670 | 0.670 | 0.670 | 0.670 | 0.670 | 0.670 |
| Polymethylsilsesquioxane | 0.250 | 0.250 | 0.250 | 0.250 | 0.250 | 0.250 |
| Cetearyl glucoside + cetearyl alcohol | 0.200 | 0.200 | 0.200 | 0.200 | 0.200 | 0.200 |
| Behenyl alcohol | 0.400 | 0.400 | 0.400 | 0.400 | 0.400 | 0.400 |
| Ethylparaben | 0.200 | 0.200 | 0.200 | 0.200 | 0.200 | 0.200 |
| Propylparaben | 0.100 | 0.100 | 0.100 | 0.100 | 0.100 | 0.100 |
| Cetyl alcohol | 0.320 | 0.320 | 0.320 | 0.320 | 0.320 | 0.320 |
| Stearyl alcohol | 0.480 | 0.480 | 0.480 | 0.480 | 0.480 | 0.480 |
| Tocopheryl acetate | 0.500 | 0.500 | 0.500 | 0.500 | 0.500 | 0.500 |
| PEG-100 stearate | 0.100 | 0.100 | 0.100 | 0.100 | 0.100 | 0.100 |
| Glycerine | 7.000 | 7.000 | 7.000 | 7.000 | 7.000 | 7.000 |
| Titanium dioxide | 0.604 | 0.604 | 0.604 | 0.604 | 0.604 | 0.604 |
| Polyacrylamide + C13-14 isoparaffin + laureth-7 | 3.000 | 2.000 | 2.000 | 2.000 | 2.000 | 2.000 |
| Panthenol | 1.000 | 1.000 | 1.000 | 1.000 | 1.000 | 1.000 |
| Benzyl alcohol | 0.400 | 0.400 | 0.400 | 0.400 | 0.400 | 0.400 |
| Dimethicone + dimethiconol | 2.000 | 2.000 | 2.000 | 2.000 | 2.000 | 2.000 |
| Water (to 100 g) | to 100 | to 100 | to 100 | to 100 | to 100 | to 100 |
| TOTAL | 100 | 100 | 100 | 100 | 100 | 100 |

Example 9

Hair-care Formulation

Content in g of component per 100 g of formulation

| Component | G | H | I |
|---|---|---|---|
| Disodium EDTA | 0.100 | 0.100 | 0.100 |
| Oxynex ® ST | 2.000 | 2.000 | 2.000 |
| Dye A, B, C, or D or dye combination comprising A, B, C, or D | 0.20 | 1.500 | 0.75 |
| Cetyl pyridinium chloride | 0.200 | 0 | 0 |
| Pitera ® | 0 | 10 | 0 |
| Ascorbyl glycoside | 0 | 0 | 2.000 |
| Niacinamide | 3.500 | 5.000 | 4.000 |
| Polyquaternium 37 | 0 | 0 | 0 |
| Isohexadecane | 3.000 | 2.500 | 2.000 |
| Isopropyl isostearate | 1.330 | 1.330 | 1.330 |
| Sucrose polycottonseedate | 0.670 | 0.670 | 0.670 |
| Polymethylsilsesquioxane | 0.250 | 0.250 | 0.250 |
| Cetearyl glucoside + cetearyl alcohol | 0.200 | 0.200 | 0.200 |
| Behenyl alcohol | 0.400 | 0.400 | 0.400 |
| Ethylparaben | 0.200 | 0.200 | 0.200 |
| Propylparaben | 0.100 | 0.100 | 0.100 |
| Cetyl alcohol | 0.320 | 0.320 | 0.320 |
| Stearyl alcohol | 0.480 | 0.480 | 0.480 |
| Tocopheryl acetate | 0.500 | 0.500 | 0.500 |
| PEG-100 stearate | 0.100 | 0.100 | 0.100 |
| Glycerine | 7.000 | 7.000 | 7.000 |
| Titanium dioxide | 0.604 | 0.604 | 0.604 |
| Polyacrylamide + C13-14 isoparaffin + laureth-7 | 2.000 | 2.000 | 2.000 |
| Panthenol | 1.000 | 1.000 | 1.000 |
| Benzyl alcohol | 0.400 | 0.400 | 0.400 |
| Dimethicone + dimethiconol | 2.000 | 2.000 | 2.000 |
| Water (to 100 g) | to 100 | to 100 | to 100 |
| TOTAL | 100 | 100 | 100 |

Example 10

O/W Emulsions

| Emulsion | A | B | C | D | E | F |
|---|---|---|---|---|---|---|
| Glyceryl stearate citrate | 2.5 | 2 | 3 | | | |
| Sorbitan stearate | 0.5 | | | 2 | 1.5 | 2 |
| Polyglyceryl-3 methylglucose distearate | | | | 2.5 | 3 | 3 |
| Polyglyceryl-2 dipolyhydroxystearate | | 0.8 | | | | 0.5 |
| Cetearyl alcohol | | | 1 | | | |
| Stearyl alcohol | 2 | | | | | 2 |
| Cetyl alcohol | | 1 | | | 3 | |
| Acrylates/C$_{10-30}$ Alkyl Acrylate Crosspolymer | | 0.2 | | | 0.1 | |
| Carbomer | | 0.2 | 0.3 | 0.2 | | |
| Xanthan Gum | 0.4 | | 0.2 | 0.2 | 0.3 | 0.4 |
| C$_{12-15}$ alkyl benzoate | 5 | 3 | | | 5 | |
| C$_{12-13}$ alkyl tartrate | | 2 | | | | |
| Butylene glycol dicaprylate/dicaprate | 5 | | | | 3 | 3 |
| Dicaprylyl Ether | | | | | 2 | |
| Octyldodecanol | 2 | | | | | |
| Dicapryl caprate | | 2 | | | 2 | 2 |
| Cyclomethicone | 5 | | 5 | 10 | | |
| Dimethicone | | | | 5 | | |
| Isohexadecane | | 1 | | | | |
| Butylene glycol | 5 | 8 | | | | 3 |
| Propylene gycol | | | 1 | | 5 | 3 |
| Glycerine | 3 | 5 | 7 | 10 | 3 | 3 |
| C18-C38 acid triglycerides | 0.5 | | 1 | | 1 | |
| Titanium dioxide | 5 | | | 2 | | |
| 2,2'-Methylenebis(6-(2H-benzotriazol-2-yl)-(1,1,3,3-tetramethylbutyl)phenol) | 2.5 | | | | | |
| 2,4,6-Tris(biphenyl)-1,3,5-triazine | | 2 | | | | |
| Merocyanine coupled to gelatine | 6 | | 6 | | 10 | 3 |
| Benzotriazole coupled to gelatine | | 5 | | 10 | | 3 |
| C8-C16 alkylpolyglycoside | 1 | 0.6 | | | | |
| UVASorb ® K2A | | | 2 | | | |
| Uvinul ® A Plus | 2 | | | | | 1 |
| Homosalate | | 5 | | 1 | | |
| Phenylbenzimidazolesulfonic acid | | | 2 | | | 1 |
| Benzophenone-3 | 0.5 | | | | 1 | |
| Octyl salicylate | 5 | 5 | | 2 | | |
| Octocrylene | 2 | | | | 3 | 1 |
| Dye A | 0.1 | 0.2 | 0.3 | 0.4 | 0.5 | 1.0 |
| Dye B | 0.1 | 0.2 | 0.3 | 0.4 | 0.5 | 1.0 |
| Bis-ethylhexyloxyphenol methoxyphenyltriazine | | 3 | 2 | 1 | | |
| Parsol ® SLX | | | | 3 | | |
| Dihydroxyacetate | | | | | 4 | |
| Taurine | 0.1 | | | 0.5 | 0.2 | |
| 8-Hexadecene-1,16-dicarboxylic acid | | 0.2 | | | | |
| Vitamin E acetate | 0.2 | 0.2 | | 0.3 | 0.1 | 0.5 |
| Na$_2$H$_2$EDTA | 0.1 | 0.1 | 0.2 | 0.2 | 0.2 | 0.5 |
| Perfume, preservative | q.s. | q.s. | q.s. | q.s. | q.s. | q.s. |
| Dyes, etc. | q.s. | q.s. | q.s. | q.s. | q.s. | q.s. |
| Sodium hydroxide | q.s. | q.s. | q.s. | q.s. | q.s. | q.s. |
| Water | to 100.0 | to 100.0 | to 100.0 | to 100.0 | to 100.0 | to 100.0 |

Example 11

O/W Emulsions

| Emulsion | G | H | I | K | L | M |
|---|---|---|---|---|---|---|
| Ceteareth-20 | 1 | 1.5 | 1 | | | |
| Sorbitan stearate | | | | 0.5 | 0.5 | |
| Glyceryl Stearate SE | | | | 1 | 1 | 1.5 |
| Emulgade F ® | | | | 2.5 | 2.5 | 3 |
| Cetearyl alcohol | | | | 1 | | |
| Stearyl alcohol | | | | | 1.5 | |
| Cetyl alcohol | | | 0.5 | | | 2 |
| Acrylates/C$_{10-30}$ Alkyl Acrylate Crosspolymer | 0.2 | 0.4 | 0.3 | 0.1 | | |
| Carbomer | | | | | 0.3 | |
| Xanthan Gum | | | | 0.4 | | 0.4 |
| C$_{12-15}$ alkyl benzoate | 5 | 3 | | | 5 | |
| 2-Phenyl benzoate | | | 2 | | | |
| Butylene glycol dicaprylate/dicaprate | 5 | | | | 3 | 2 |
| Dicaprylyl Ether | | | | | 2 | |
| Diethylhexyl naphthalate | 2 | | | | | |
| Dicapryl caprate | | 2 | | | 2 | 2 |
| Cyclomethicone | 5 | | 5 | 10 | | |
| Isohexadecane | | | | | 5 | |
| Mineral oil | | 1 | | | | |
| Propylene glycol | | | 4 | | | |
| Glycerine | 5 | 7 | 3 | 5 | 6 | 8 |
| C18-38 acid triglycerides | 0.5 | | 1 | | 1 | |
| Titanium dioxide | 5 | | 3 | 2 | | |
| Phenylbenzimidazole-sulfonic acid | 1 | | | 1 | 2 | 1 |

| Emulsion | G | H | I | K | L | M |
|---|---|---|---|---|---|---|
| Parsol ® SLX | 0.5 | 1.0 | 1.5 | 2.0 | 2.5 | 3.0 |
| Dye A | 0.5 | 1.0 | 3.0 | 0.5 | | |
| Dye B | | | 0.5 | 3.0 | 1.0 | 0.5 |
| Creatinine | 0.1 | 0.01 | 0.05 | | | |
| Creatine | 0.5 | 0.2 | 0.1 | | | |
| Liquorice extract/licochalcone | | | | 0.5 | | |
| Vitamin E acetate | 0.2 | | | 0.5 | 0.5 | 0.5 |
| Tapioca starch | | 3 | | | 2 | |
| Na$_2$H$_2$EDTA | 0.1 | | 0.2 | | | 0.5 |
| Perfume, preservative | q.s. | q.s. | q.s. | q.s. | q.s. | q.s. |
| Pigment dyes | q.s. | q.s. | q.s. | q.s. | q.s. | q.s. |
| Sodium hydroxide | q.s. | q.s. | q.s. | q.s. | q.s. | q.s. |
| Water | to 100.0 | to 100.0 | to 100.0 | to 100.0 | to 100.0 | to 100.0 |

Example 12

O/W Emulsions for Skin Colouring with UV Protection

| Emulsion | N | O | P | Q | R | S |
|---|---|---|---|---|---|---|
| Glyceryl stearate SE | | 2 | | 2 | | |
| Glyceryl stearate | 2 | | 2 | | | |
| PEG-40 stearate | | | 2 | | 1 | |
| PEG-10 stearate | | | | 2.5 | 1 | |
| Ceteareth-20 | | | | | | 2.6 |
| Sodium Cetyl Phosphate | | | | | 2 | |
| Glyceryl Stearate, Ceteareth-12, Ceteareth-20, Cetearyl Alcohol, Cetyl Palmitate | | | | | | 5.4 |
| Stearic acid | 3 | 2 | | | 2 | |
| Stearyl alcohol | | 2 | 2 | | | |
| Stearyl alcohol | 0.5 | | 2 | | | |
| Cetyl alcohol | 3 | | | 2 | | |
| Acrylates/C$_{10-30}$ Alkyl Acrylate Crosspolymer | | | 0.2 | | 0.4 | |
| Carbomer | | 0.3 | | 0.3 | 0.3 | |
| Xanthan Gum | | 0.3 | 0.4 | | | |
| C$_{12-15}$ alkyl benzoate | 5 | | | | 5 | 3 |
| 2-Phenyl benzoate | 5 | | | | | |
| Butylene glycol dicaprylate/dicaprate | | 5 | | 4 | | 3 |
| Dicaprylyl Ether | | 2 | | | 3 | |
| Diethylhexyl naphthalate | 3 | | | | | |
| Cyclomethicone | 2 | | 10 | 2 | | |
| Isohexadecane | | | | 2 | 3 | |
| Mineral oil | | | | | 3 | |
| Propanediol | | 3 | | 5 | | |
| Glycerine | 3 | 5 | 10 | 7 | 4 | 5 |
| Titanium dioxide | 2 | 4 | | | | |
| Zinc oxide | | | | | 2 | |
| Drometrizole Trisiloxane | | | | | 3 | |
| Ethylhexyl methoxy-cinnamate | | 6 | 5 | | | |
| Phenylbenzimidazolesulfonic acid | | 0.5 | 2 | | 1 | |
| Homosalate | 5 | | | 7 | | |
| Butyl methoxydibenzoyl-methane | | 3 | | | | |
| Bis-Ethylhexyloxyphenol Methoxyphenyltriazine | | 2 | 3 | | | |
| Octyl salicylate | | | | | 5 | |
| Octocrylene | | | | | 3 | |
| Dye A | 0.25 | 0.5 | 0.75 | 1.0 | 1.25 | 1.5 |
| Parsol ® SLX | 4 | | | | | 5 |
| PVP hexadecene copolymer | 0.5 | | 1 | | 0.8 | |
| Coenzyme Q 10 | 0.2 | 0.02 | | 0.3 | | |
| Vitamin E acetate | 0.2 | | 0.3 | | 0.8 | 0.5 |
| Na$_2$H$_2$EDTA | 0.1 | | | | | 0.5 |
| Perfume, preservative | q.s. | q.s. | q.s. | q.s. | q.s. | q.s. |
| Pigment dyes | q.s. | q.s. | q.s. | q.s. | q.s. | q.s. |
| Sodium hydroxide | q.s. | q.s. | q.s. | q.s. | q.s. | q.s. |
| Water | to 100.0 | to 100.0 | to 100.0 | to 100.0 | to 100.0 | to 100.0 |

Example 13

Aqueous and Aqueous/Alcoholic Formulations

| | A | B | C | D | E | F |
|---|---|---|---|---|---|---|
| Ethanol | 50 | 5 | 2 | 40 | 15 | |
| Hydroxyethylcellulose | 0.5 | | | | | |
| Acrylates/C10-30 Alkyl Acrylate Crosspolymer | | | | 0.3 | 0.6 | |
| Cocoatnidopropyl-betaine | | | 0.3 | | | |
| UVASorb ® K2A | | | | | 2 | |
| Uvinul ® APlus | 5 | | | | | |
| Butyl methoxydibenzoyl-methane | 0.5 | | | 3 | | |
| Disodium phenyl-dibenzimidazoletetra-sulfonate | | 2 | 1 | | | |
| Phenylbenzimidazole-sulfonic acid | | 5 | 3 | | 2 | 4 |
| Dye A | 0.1 | 0.25 | 0.5 | 1 | 2 | 3 |
| Dye B | 3 | 2 | 1 | 0.5 | 0.25 | 0.1 |
| Dye C | 0.1 | 0.25 | 0.5 | 1 | 2 | 3 |
| Dye D | 3 | 2 | 1 | 0.5 | 0.25 | 0.1 |
| $C_{12-15}$ alkyl benzoate | | | | 3 | | |
| C18-36 triglyceride fatty acid | | | | 1 | | |
| Butylene glycol dicaprylate/dicaprate | 2 | | | | | |
| C12-13 alkyl tartrate | | | | | 5 | |
| Cyclomethicone | 4 | | | 2 | | |
| Insect repellent ® 3535 | | | | 5 | | |
| Dimethicone | | | | | 3 | |
| PVP hexadecene copolymer | | 0.5 | | 1 | | 0.5 |
| Ethylhexyloxy-glycerine | | 0.5 | | | | |
| Glycerine | 5 | 7 | 3 | 8 | | S |
| Butylene glycol | | | 5 | | 5 | |
| Metylpropanediol | | | | 4 | | |
| Vitamin E acetate | | 0.3 | 0.2 | 0.5 | | |
| Panthenol | 0.5 | | 0.2 | | | 0.3 |
| Creatinine | | | 0.01 | | 0.02 | |
| Creatine | | | 0.1 | | 0.2 | |
| PEG-40 hydrogenated castor oil | | 0.5 | 0.3 | | | 0.5 |
| Trisodium EDTA | 0.3 | 0.2 | 0.2 | 0.2 | 0.2 | 0.5 |
| Preservative | q.s. | q.s. | q.s. | q.s. | q.s. | q.s. |
| Sodium hydroxide | q.s. | q.s. | q.s. | q.s. | q.s. | q.s. |
| Perfume, dyes | q.s. | q.s. | q.s. | q.s. | q.s. | q.s. |
| Water | to 100 | to 100 | to 100 | to 100 | to 100 | to 100 |

Example 14

Cosmetic Foams

| Emulsion | A | B | C |
|---|---|---|---|
| Stearic acid | 2 | 2 | |
| Palmitic acid | | | 1.5 |
| Cetyl alcohol | 2.5 | 2 | |
| Stearyl alcohol | | | 3 |
| PEG-100 stearate | | | 3.5 |
| PEG-40 stearate | | 2 | |
| PEG-20 stearate | 3 | | |
| Sorbitan stearate | | | 0.8 |
| $C_{12-15}$ alkyl benzoate | 5 | | |
| $C_{12-13}$ alkyl tartrate | | | 7 |
| Butylene glycol dicaprylate/dicaprate | | 6 | |
| Dicaprylyl Ether | | | 2 |
| Cyclomethicone | | 2 | 3 |
| Butylene glycol | 1 | | |
| Isohexadecane | 2 | | |
| Methylpropanediol | | | |
| Propylene glycol | | | 5 |
| Glycerine | 5 | 7 | |
| UVASorb ® K2A | | | 2 |
| Uvinul ® A Plus | 2 | 3 | |
| Parsol SLX ® | | 3 | |
| Dye A | 1.0 | | |
| Dye B | | 2.0 | |
| Dye C | | | 1.5 |
| Dye D | | | 1.5 |
| Octocrylene | 2 | | |
| Bis-Ethylhexyloxyphenol Methoxyphenyltriazine | | 3 | |
| 2,2'-Methylenebis(6-(2H-benzotriazol-2-yl)-4-(1,1,3,3-tetramethylbutyl)phenol) | | | 8 |
| 2,4,6-Tris-(biphenyl)-1,3 5-triazine | 5 | | 4 |
| C8-C16 alkylpolyglycosides | 1 | | |
| Vitamin E acetate | 0.6 | 0.5 | 0.2 |
| Creatine/creatinine | | | 0.5 |
| BHT | | | 0.1 |
| $Na_2H_2EDTA$ | 0.50 | | |
| Perfume, preservative | q.s. | q.s. | q.s. |
| Dyes, etc. | q.s. | q.s. | q.s. |
| Sodium hydroxide | q.s. | q.s. | q.s. |
| Potassium hydroxide | | q.s. | |
| Water | to 100.0 | to 100.0 | to 100.0 |

Example 15

Cosmetic Foams

| Emulsion | D | E | F | G |
|---|---|---|---|---|
| Stearic acid | 2 | | | |
| Palmitic acid | | | 3 | 3 |
| Cetyl alcohol | 2 | 2 | | |
| Cetylstearyl alcohol | | | 2 | 2 |
| Stearyl alcohol | | | | |
| PEG-100 stearate | | 4 | | |
| PEG-40 stearate | 2 | | | |
| PEG-20 stearate | | | 3 | 3 |
| Sorbitan stearate | 0.8 | | | |
| Tridecyl Trimellitate | | 5 | | |
| $C_{12-15}$ alkyl benzoate | | | 3 | 3 |
| Butylene glycol dicaprylate/dicaprate | 8 | | | |
| Octyldodecanol | | 2 | | |
| Cocoglyceride | | | | 2 |
| Dicaprylyl Ether | | | 2 | 2 |
| Cyclomethicone | | | | |
| Dimethicone | 1 | | 2 | 2 |
| Isohexadecane | | 3 | | |
| Methylpropanediol | | 4 | | |
| Propylene glycol | | | | |
| Glycerine | 5 | | 6 | 6 |
| NeoHeliopan ® AP | | 2 | | |
| Phenylbenzimidazole-sulfonic acid | 1 | | | 1 |
| Dye A | 0.5 | 0.5 | 0.5 | 0.5 |
| Ethylhexyl methoxy-cinnamate | 5 | | 4 | 4 |
| Ethylhexyltriazone | | 2 | | 1 |

-continued

| Emulsion | D | E | F | G |
|---|---|---|---|---|
| Eusolex T-AVO ® | 2 | | | |
| Diethylhexylbutamido-triazone | 1 | | | |
| Butylmethoxydibenzoyl-methane | 2.5 | | 2 | 2 |
| Bis-Ethylhexyloxyphenol Methoxyphenyltriazine | 2 | | | |
| Vitamin E acetate | 0.2 | | 0.3 | 0.3 |
| Na$_2$H$_2$EDTA | | | | |
| Perfume, preservative | | | | |
| Dyes, etc. | | | | |
| Sodium hydroxide | | q-s. | q.s. | |
| Triethanolamine | q.s. | | | q.s. |
| Water | to 100.0 | to 100.0 | to 100.0 | to 100.0 |

Example 16

Hair-colouring Test, Colour Intensity

Phenylazobenzoic acid 6O-L-ascorbate (PABA, dye A) is investigated with respect to its hair-colouring action compared with phenylazobenzoic acid (PABS), which has an identical chromophore. To this end, white strands of hair from buffalo stomach are firstly incubated with water for 60 minutes (=experiment variant A). The hair strands are subsequently soaked with in each case 10% aqueous dispersions of the dyes PABA and PABS. After removal, the hair strands are subsequently wrapped in aluminium foil and stored at 45° C. for 20 hours. The hair is subsequently rinsed with water and dried using a hairdryer. The hair strands coloured in this way are then washed with shampoo five times one after the other. In the case of treatment with PABA, an intense yellow-orange colouration is achieved, while PABS has virtually no colouring action.

In a parallel batch (=experiment variant B), the incubation is carried out with 10% ammonia solution instead of water, and excess ammonia solution is rinsed out with water before the colouring step.

The respective colour effect is recorded chromametrically against untreated hair (evaluation in accordance with CIE-L*a*b, DIN6174). All measurement values are recorded with the aid of a Varian Cary50 spectrophotometer in combination with the colour analysis software version 3.10 (228). The remission measurement probe used is the Harrick, Barellino model (Serial No BRLVA358431109019, wavelength range 360-830 nm, interval 1 nm, observation angle 2°, illumination CIED65, base line correction against white standard (barium sulfate)).

Measurement Values:

Experiment Variant A

| | ΔL | Δa | Δb |
|---|---|---|---|
| Ascorbic acid dye PABA | −7.72 | 6.13 | 45.1 |
| Comparative dye PABS | −11.7 | −0.46 | 23.6 |

Experiment Variant B

| | ΔL | Δa | Δb |
|---|---|---|---|
| Ascorbic acid dye PABA | −11.9 | 8.80 | 44.9 |
| Comparative dye PABS | −2.35 | −2.13 | 25.4 |

It can be read off from the results tables that very much stronger red and yellow colour values are achieved for the colourings with the ascorbic acid dye PABA compared with PABS, which has an identical chromophore.

The invention claimed is:
1. A compound of the formula I

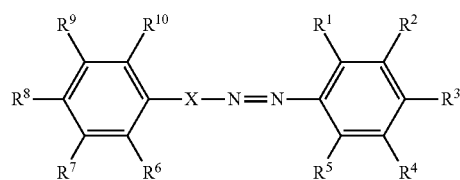

where X stands for a single bond or a substituent of the formula IIa or IIb

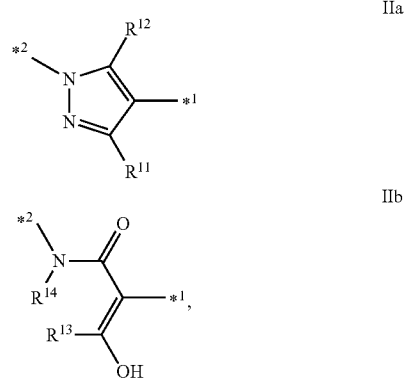

where *$^1$ is oriented towards the N═N,
where:
  when X is a single bond, precisely one of the substituents R$^1$ to R$^{10}$ stands for a substituent of the formula IIIa, IIIb or IIIc;
  when X is of formula IIa, precisely one of the substituents R$^1$ to R$^{12}$ stands for a substituent of the formula IIIa, IIIb or IIIc; and
  when X is of formula IIb, precisely one of the substituents R$^1$ to R$^{10}$, R$^{13}$ or R$^{14}$ stands for a substituent of the formula IIIa, IIIb or IIIc;

-continued

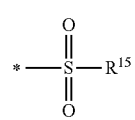
IIIb

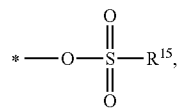
IIIc where $R^{15}$ in each case stands, independently of one another, for an ascorbic acid radical of the formula IVa or IVb or a dehydroascorbic acid radical of the formula IVc or IVd, in each case as the L or D enantiomer,

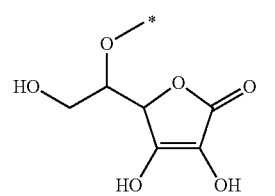
IVa

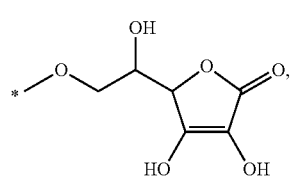
IVb

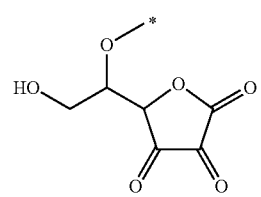
IVc

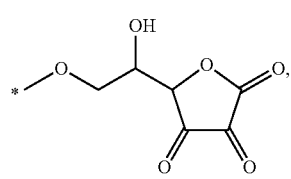
IVd where the remaining substituents $R^1$ to $R^{14}$ each stand, independently of one another, for H, OH, $NH_2$, $NO_2$, F, Cl, Br, I, $CF_3$, $OCF_3$, $O(C=O)-CH_2-NH_2$, $Alk^1$, $OAlk^1$, $NHAlk^1$, $NAlk^1_2$, Cyc, $(NAlk^1_3)^+_x An^{x-}$, $(SO_2)NH_2$, $(SO_2)NHAlk^1$, $O(SO_2)OAlk^1$, $O(SO_2)OArl$, $(C=O)OAlk^1$, $(C=O)OArl$ or Arl, where $Alk^1$ in each case stands, independently of one another, for a straight-chain or branched $C_1$- to $C_{20}$-alkyl group or for a straight-chain or branched $C_2$- to $C_{20}$-alkenyl group, which may have a plurality of double bonds, where at least one C atom or a plurality of non-adjacent C atoms of the $C_1$- to $C_{20}$-alkyl or $C_2$- to $C_{20}$-alkenyl group may be replaced by O, and where the $C_1$- to $C_{20}$-alkyl or $C_2$- to $C_{20}$-alkenyl group may have at least one OH, F, Cl, Br or I bonded to a primary or secondary C atom, where Arl in each case stands, independently of one another, for an unsubstituted, mono- or polysubstituted $C_6$- to $C_{20}$-aryl group, where Cyc stands for a $C_3$- to $C_8$-cycloalkyl group, which may have at least one double bond and/or in which at least one $CH_2$ may be replaced by O or NH, where $An^{x-}$ in each case stands, independently of one another, for an anion having the charge $1 \leq x \leq 3$ or a tautomer or stereoisomer thereof, including mixtures thereof in all ratios.

2. A compound according to claim 1, wherein the remaining substituents $R^1$ to $R^{14}$ each stand, independently of one another, for H, OH, $NH_2$, $NO_2$, F, Cl, Br, I, $CF_3$, $OCF_3$, $Alk^1$, $OAlk^1$, $NHAlk^1$, $NAlk^1_2$, $(NAlk^1_3)^+_x An^{x-}$, $(SO_2)NH_2$, $(SO_2)NHAlk^1$, $(C=O)OAlk^1$, $(C=O)OArl$ or Arl.

3. A compound according to claim 1, wherein the remaining substituents $R^1$ to $R^{14}$ each stand, independently of one another, for H, OH, $N(Alk^1)_2$, $Alk^1$, $N(Alk^1)_3 An^-$ or Arl.

4. A compound according to claim 1, wherein the remaining substituents $R^1$ to $R^{14}$ each stand, independently of one another, for H or $N(Alk^1)_2$.

5. A compound according to claim 1, wherein precisely one of the substituents $R^1$ to $R^5$ or precisely one of the substituents $R^6$ to $R^{10}$ stands for a substituent of the formula IIIa, IIIb or IIIc.

6. A compound according to claim 1, wherein precisely one of the substituents $R^1$ to $R^5$ or precisely one of the substituents $R^6$ to $R^{10}$ stands for a substituent of the formula IIIa or IIIb.

7. A process for the preparation of a compound of the formula I according to claim 1, which comprises reacting, in an esterification step, precisely one acid group of the formula VIIa, VIIb or VIIc of an azo compound of the formula V,

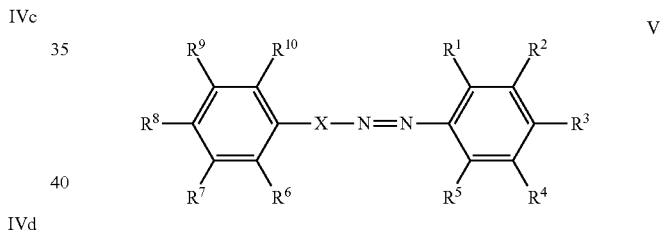
V where X stands for a single bond or a substituent of the formula VIa or VIb

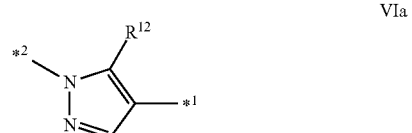
VIa

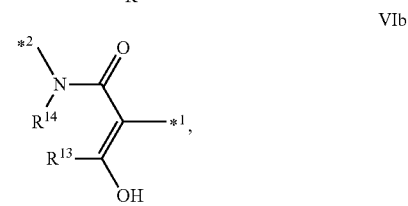
VIb where $*^1$ is oriented towards the N=N,
where:
when X is a single bond, precisely one of the substituents $R^1$ to $R^{10}$ stands for an acid group of the formula VIIa, VIIb or VIIc;

when X is of formula VIa, precisely one of the substituents $R^1$ to $R^{12}$ stands for an acid group of the formula VIIa, VIIb or VIIc; and when X is of formula VIb, precisely one of the substituents $R^1$ to $R^{10}$, $R^{13}$ or $R^{14}$ stands for an acid group of the formula VIIa, VIIb or VIIc;

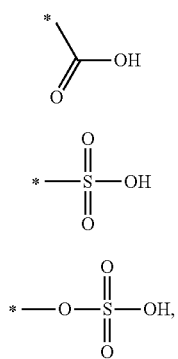

where remaining substituents $R^1$ to $R^{14}$ have a meaning described in claim 1;

with precisely one hydroxyl group in the fifth or sixth position of the ascorbic acid which provides the ascorbic acid radical of the formula IVa or IVb or dehydroascorbic acid which provides the dehydroascorbic acid radical of the formula IVc or IVd.

8. The process according to claim 7, further comprising, in addition to the esterification step, at least one of the following process steps:
   a) an activation step in which the acid group of the formula VIIa, VIIb or VIIc is activated for a subsequent esterification,
   b) a protection of at least one hydroxyl group in the fifth or sixth position of the ascorbic acid or dehydroascorbic acid by means of a first protecting group,
   c) a protection of at least one hydroxyl group in the second or third position of the ascorbic acid by a second protecting group, or
   d) a removal of at least one first or second protecting group, where the first and second protecting groups can be cleaved off under different reaction conditions.

9. A method of dying a matrix comprising adding to the matrix a compound of claim 1 and/or a salt thereof.

10. A method according to claim 9, wherein the matrix is hair, skin, nails, textiles and/or plastic.

11. A method according to claim 9, wherein at least two compounds of the formula I are used, where the compounds differ with respect to $R^{15}$ and $R^{15}$ stands for an ascorbic acid radical of the formula IVa or IVb or for a dehydroascorbic acid radical of the formula IVc or IVd, in each case as the L or D enantiomer.

12. A process for the colouring of a matrix in which the matrix is coloured directly, in a colouring step, by the action of a dispersion and/or solution and/or emulsion of a compound of the formula I according to claim 1 on the matrix.

13. A process according to claim 12, wherein the matrix is treated by means of a pretreatment agent in a pre-treatment step in order to influence the colouring behaviour.

14. A composition comprising at least one compound of the formula I according to claim 1 and at least one further vehicle suitable for a cosmetic, pharmaceutical, dermatological or household product composition.

15. A process for the preparation of a composition according to claim 14 comprising mixing at least one compound of the formula I with at least one vehicle which is suitable for cosmetic, pharmaceutical, dermatological compositions or household products and optionally assistants and/or fillers.

16. The process according to claim 7, further comprising, in addition to the esterification step, at least one of the following process steps:
   a) an activation step carried out before the esterification step in which the acid group of the formula VIIa, VIIb or VIIc is activated for a subsequent esterification,
   b) a protection carried out before the esterification step or activation step of at least one hydroxyl group in the fifth or sixth position of the ascorbic acid or dehydroascorbic acid by means of a first protecting group,
   c) a protection carried out before the esterification step or activation step of at least one hydroxyl group in the second or third position of the ascorbic acid by a second protecting group, or
   d) a removal carried out after the esterification step of at least one first or second protecting group, where the first and second protecting groups can be cleaved off under different reaction conditions.

17. A method of dying a protein-containing matrix, comprising adding to the matrix a compound of claim 1 and/or a salt thereof.

18. Process for the colouring of a protein-containing matrix, in which the matrix is coloured directly, in a colouring step, by the action of a dispersion and/or solution and/or emulsion of a compound of the formula I according to claim 1 on the matrix.

19. A process for the preparation of a composition according to claim 14 comprising mixing to disperse, emulsify or dissolve at least one compound of the formula I with at least one vehicle which is suitable for cosmetic, pharmaceutical, dermatological compositions or household products and optionally assistants and/or fillers.

20. A composition according to claim 14, wherein the at least one compound of the formula I is contained in the composition in an amount of 0.05 to 10% by weight.

* * * * *